(12) United States Patent
Busold et al.

(10) Patent No.: US 10,052,107 B2
(45) Date of Patent: Aug. 21, 2018

(54) SYSTEMS AND METHODS FOR THE TREATMENT OF ANEURYSMS

(71) Applicant: ARSENAL MEDICAL, INC., Watertown, MA (US)

(72) Inventors: Rany Busold, Medford, MA (US); John Marini, Weymouth, MA (US); Upma Sharma, Somerville, MA (US); Adam Rago, Falmouth, MA (US); Jennifer Mortensen, Somerville, MA (US); Joseph Lomakin, Cambridge, MA (US); Gregory T. Zugates, Chelmsford, MA (US); Janet Komatsu, Cambridge, MA (US); Jeffrey Groom, III, Medford, MA (US)

(73) Assignee: ARSENAL MEDICAL, INC., Watertown, MA (US)

( * ) Notice: Subject to any disclaimer, the term of this patent is extended or adjusted under 35 U.S.C. 154(b) by 0 days.

(21) Appl. No.: 14/212,930

(22) Filed: Mar. 14, 2014

(65) Prior Publication Data
US 2016/0256170 A1 Sep. 8, 2016
US 2018/0177507 A9 Jun. 28, 2018

Related U.S. Application Data

(63) Continuation-in-part of application No. 13/532,013, filed on Jun. 25, 2012.
(Continued)

(51) Int. Cl.
*A61F 2/06* (2013.01)
*A61B 17/12* (2006.01)
*A61F 2/07* (2013.01)

(52) U.S. Cl.
CPC .... *A61B 17/12118* (2013.01); *A61B 17/1219* (2013.01); *A61B 17/12186* (2013.01);
(Continued)

(58) Field of Classification Search
CPC .... A61L 31/06; A61L 24/046; A61L 2400/06; A61L 31/146; A61L 24/0036;
(Continued)

(56) References Cited

U.S. PATENT DOCUMENTS

| 7,763,269 | B2 * | 7/2010 | Wright | A61B 17/00008 424/423 |
| 2002/0165582 | A1 * | 11/2002 | Porter | A61B 17/12022 606/213 |
| 2003/0059371 | A1 * | 3/2003 | Matson | A61K 49/0404 424/9.3 |
| 2005/0277864 | A1 * | 12/2005 | Haffner | A61F 9/00781 604/8 |

(Continued)

FOREIGN PATENT DOCUMENTS

| WO | 1999002092 A1 | 1/1999 |
| WO | 2003103631 A1 | 12/2003 |

(Continued)

OTHER PUBLICATIONS

International Search Report and Written Opinion for International Application No. PCT/US2014/028701 dated Sep. 22, 2014; 11 pages.

*Primary Examiner* — Katherine M Shi

(57) ABSTRACT

Systems and method for treating aneurysms are provided which utilize formulations that form polymer foams in situ. The formulations generally have a buoyancy greater than or less than blood, and either float to the top of the aneurysm and foam from the top down or sink to the bottom and foam from the bottom up.

20 Claims, 24 Drawing Sheets

Related U.S. Application Data

(60) Provisional application No. 61/852,422, filed on Mar. 15, 2013, provisional application No. 61/852,315, filed on Mar. 15, 2013.

(52) U.S. Cl.
CPC ........ *A61B 17/12195* (2013.01); *A61F 2/07* (2013.01); *A61B 2017/1205* (2013.01); *A61B 2217/005* (2013.01); *A61F 2002/077* (2013.01)

(58) Field of Classification Search
CPC ............ A61L 2300/60; A61L 2430/36; A61L 2400/04; A61L 27/56; A61L 27/58; A61L 31/14; A61L 31/148; A61F 2002/077; A61F 2/07; A61F 2210/0085; A61F 2/95; A61M 37/00
USPC ............ 604/290, 369; 623/1.11, 1.13, 1.21; 606/213, 214
See application file for complete search history.

(56) References Cited

U.S. PATENT DOCUMENTS

| | | | |
|---|---|---|---|
| 2010/0076484 A1* | 3/2010 | Riina | A61F 2/958 606/213 |
| 2012/0107439 A1* | 5/2012 | Sharma | A61J 1/2093 425/4 R |
| 2012/0259406 A1* | 10/2012 | Schreck | A61M 25/104 623/1.27 |
| 2012/0265287 A1* | 10/2012 | Sharma | A61L 31/06 623/1.11 |
| 2013/0116641 A1* | 5/2013 | Hicks | A61L 26/0085 604/319 |

FOREIGN PATENT DOCUMENTS

| | | |
|---|---|---|
| WO | 2005039442 A2 | 5/2005 |
| WO | 2012027138 A1 | 3/2012 |
| WO | 2012139054 A1 | 10/2012 |

\* cited by examiner

STATIC MIXING NOZZLE
ATTACHED TO CATHETER
OR DYNAMIC MISSING
NOZZLE

MIXING NOZZLE    CATHETER

CATHETER DESIGN TO
SUPPORT TURBULENT
FLOW LEADING TO
MIXING

CATHETER CROSS SECTION WITH BALLOON DEFLATED

CATHETER CROSS SECTION WITH BALLOON INFLATED

LONGITUDINAL SECTION OF ANEURYSM WITH
STENT GRAFT IN PLACE (DISTAL PORTION)

COVERED CONFIGURATION

RETRACTED CONFIGURATION

LUMEN VIEW

SPIRAL SHAPE

STAL SHAPE

FOLDED SHAPE

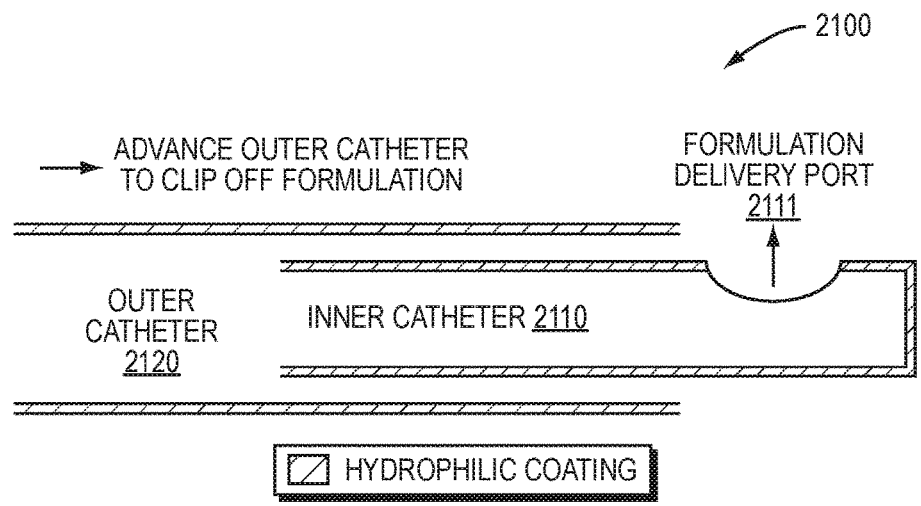
FIG. 21
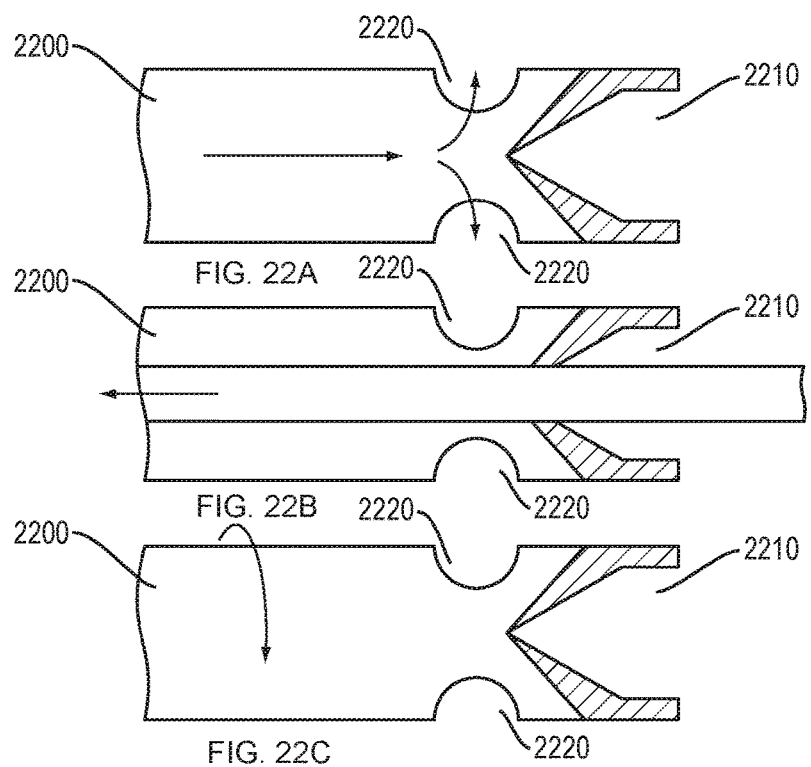
FIG. 22A
FIG. 22B
FIG. 22C

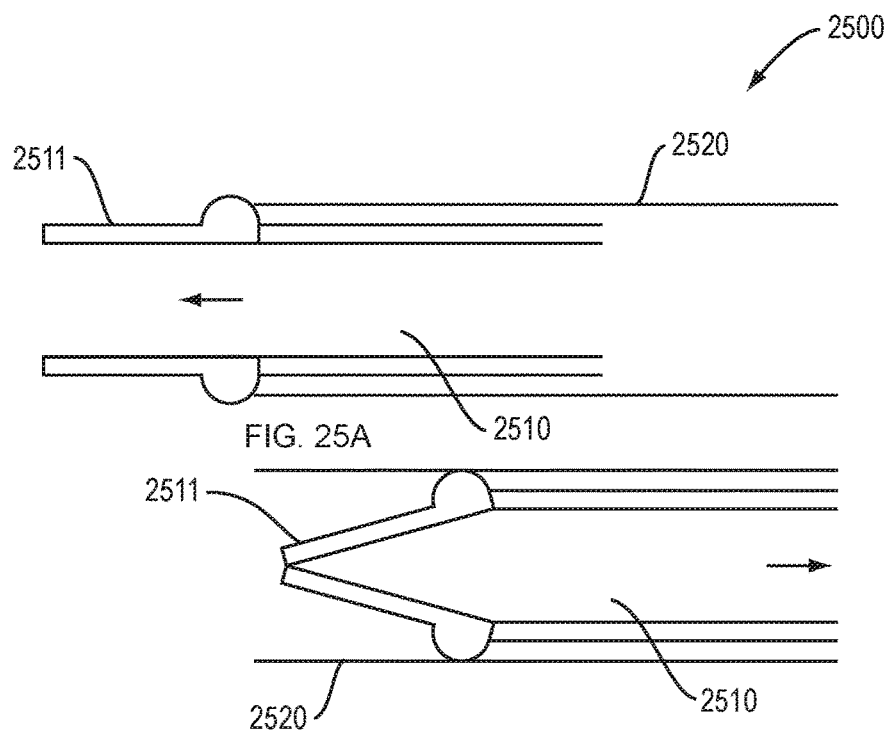
FIG. 25A
FIG. 25B
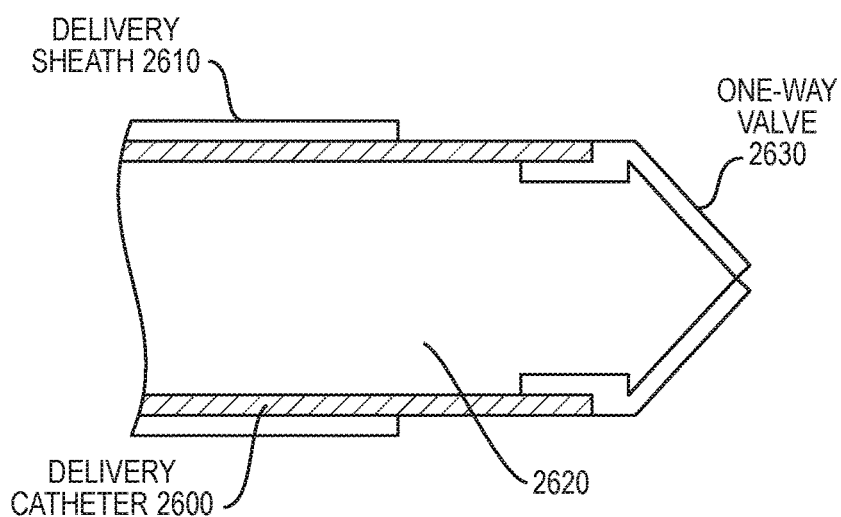
FIG. 26

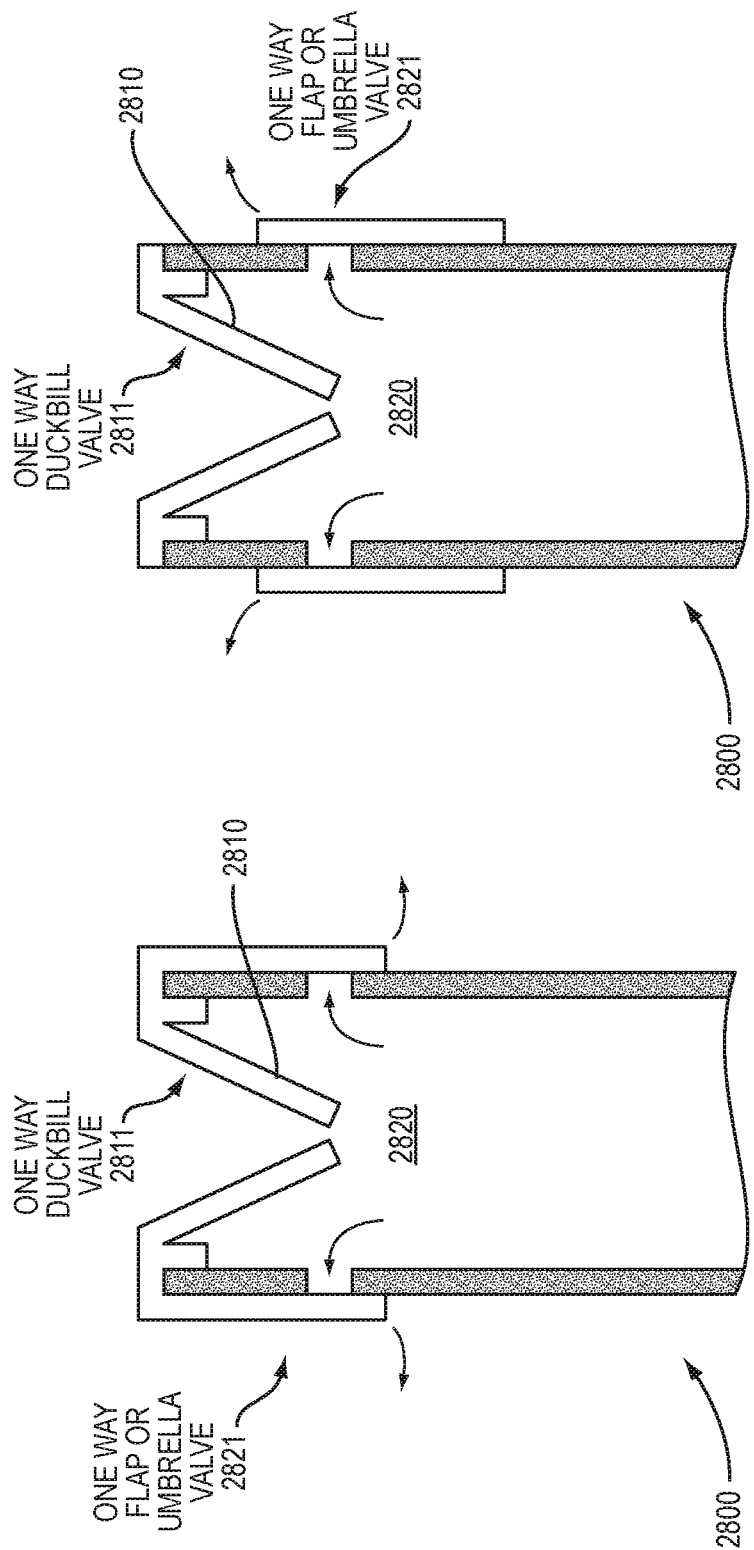

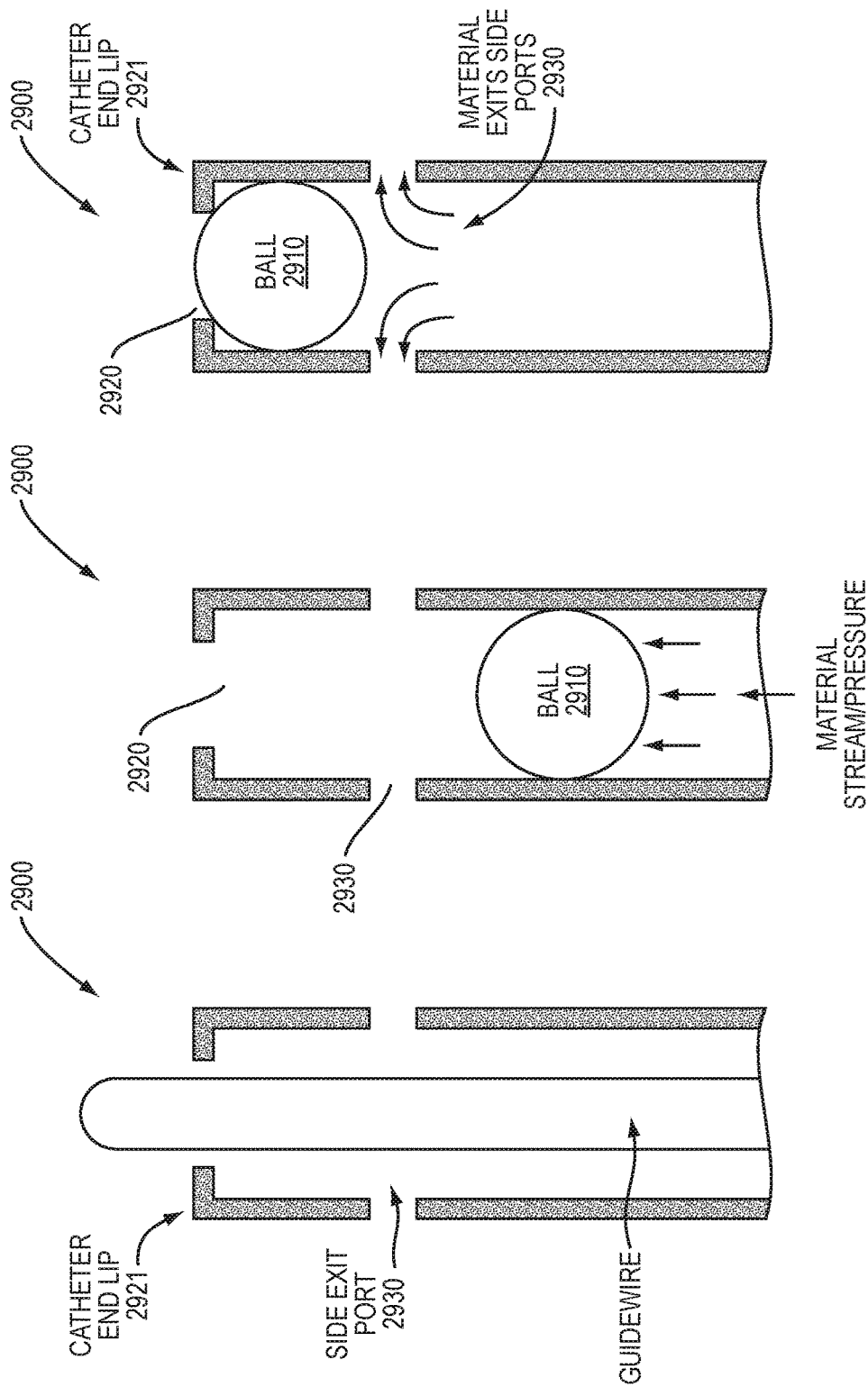

SYSTEMS AND METHODS FOR THE TREATMENT OF ANEURYSMS

CROSS-REFERENCE TO RELATED APPLICATIONS

This application claims the benefit of priority under 35 U. S. C. § 119(e) to (a) U.S. Provisional Patent Application Ser. No. 61/852,422 filed Mar. 15, 2013 and entitled "In Situ Forming Foams for Use in Fluid-Filled Spaces" and (b) U.S. Provisional Patent Application Ser. No. 61/185,315 filed Mar. 15, 2013 and entitled "Delivery Systems for In Situ Forming Foams." In addition, this application is a continuation-in-part of U.S. patent application Ser. No. 13/532,013 entitled "In-Situ Forming Foams for Treatment of Aneurysms" filed Jun. 25, 2012. The entire disclosure of each of the foregoing references is incorporated herein for all purposes.

FIELD OF THE INVENTION

Systems and methods relating to polymer foams for the treatment of aneurysms are generally described.

BACKGROUND

Early stabilization of body fluid loss can be important in the treatment of wounds and bleeding tissues. For example, many injuries are treatable if effective hemorrhage control and operative surgical intervention are undertaken rapidly. In many situations, however, immediate access to surgical care is not available. Internal wounds and bleeding sites may be particularly difficult to treat in such situations, as traditional treatment techniques (e.g., application of pressure to stop bleeding, etc.) are difficult to implement with such wounds.

Although the use of polymers in the treatment of wounds is well known in the art, previous materials and methods for treating wounds with polymers have suffered from a variety of drawbacks. For example, many polymers irritate skin and/or internal tissues. Moreover, many polymers lack suitable mechanical properties to be useful inside the body; polymers that are too stiff may lead to discomfort or further injury, while polymers that are too soft may fail to provide adequate support for internal tissues. In addition, polymers can be difficult to place within internal wounds or bleeding sites that may have complex shapes and geometries.

One clinical application in which polymers have been used to control bleeding is in the treatment of aneurysms. Generally, an aneurysm is an abnormal widening or ballooning of a portion of a blood vessel due to weakness in the vessel wall. If left untreated, aneurysms can grow large and rupture, causing internal bleeding which is often fatal. Two locations in which aneurysms are commonly found are in the abdominal aorta and the brain.

Abdominal aortic aneurysms ("AAAs") are conventionally treated by surgical removal or by endovascular repair. If the AAA is surgically repaired, a major incision is made in the abdomen or chest to access and remove and/or repair the aneurysm, and the aneurysmal segment of aorta is replaced or supplemented with a tubular graft of synthetic material such as Polyethylene terephthalate (PETE) or Polytetrafluoroethylene (PTFE). If instead it is treated by endovascular aneurysm repair ("EVAR"), the AAA is accessed via catheter using minimally invasive techniques rather than through an open surgical incision. A graft or stent-graft is delivered through the catheter and self-expands as it is expelled from the catheter to bridge the aneurysm to form a stable channel for blood flow. FIG. 1 shows an aneurysm 110 in an abdominal aorta 115 after treatment by the placement of a stent-graft 150, as is known in the art. With the increased use of EVAR in recent years, a higher incidence of endoleaks has been observed. An endoleak results from blood that is still able to access the aneurysm sac 116 after placement of the graft or stent-graft. Such a leak could be caused by an insufficient seal at the ends of the graft (referred to as a "type I" leak), retrograde flow into the aneurysm from collateral vessels (a "type II" leak), a defect in the graft (a "type III" leak), and flow through any porosity in the graft (a "type IV" leak). Such endoleaks represent a significant possible drawback to EVAR procedures as they could lead to aneurysm expansion or rupture. Endoleaks are less of a concern following surgical repair of AAA, but the surgical procedure is significantly more invasive and has higher mortality and morbidity. Thus, an improved EVAR device and system which address endoleaks would provide a significant improvement in patient care.

It has recently been proposed (Rhee et al., "Treatment of type II endoleaks with a novel polyurethane thrombogenic foam: Induction of endoleak thrombosis and elimination of intra-aneurysmal pressure in the canine model," J. Vascular Surgery 2005, 42(2): 321-8), incorporated herein by reference, to use a pre-formed polyurethane foam in the aneurysm sac following an EVAR procedure. The authors found that the use of such a foam resulted in a reduction of intra-aneurysmal pressure to a level that was indistinguishable from control aneurysms that had no endoleak. Such a pre-formed foam, however, cannot be shaped in situ to conform to the configuration of the aneurysm sac. As such, the authors were required to make use of numerous foam implants to achieve the reported results.

Likewise, it has been proposed in U.S. Publication No. 2009/0287145, incorporated herein by reference, to introduce a foam material into an aneurysm. The foam is compressible to allow for injection and then expands from its compressed configuration and hardens in situ. The foam itself, however, is pre-formed prior to injection into the aneurysm.

SUMMARY OF THE INVENTION

Systems, methods and kits relating to in situ forming polymer foams for the treatment of aneurysms are provided.

In one aspect, the present invention relates to a system for treating a patient that includes an endoprosthesis and a formulation adapted to form a polymer foam when exposed to a bodily fluid. The formulation is configured to float in blood. The formulation, in some cases, floats to the top of the aneurysm and forms a foam that expands downward to fill a volume of the aneurysm. In certain cases, the system also includes a catheter with a tip that can be placed within the aneurysm and which supplies the formulation to the aneurysm and/or removes blood that is displaced by the expansion of the foam. The catheter is, variously, sized to fit through the lumbar artery, through a fenestration within the endoprosthesis, or through a space between the endoprosthesis and the wall of a blood vessel fluidly connected to the aneurysm. The catheter may also include a retractable shield that inhibits the migration of the foam from the bottom to the top of the aneurysm, and the endoprosthesis may be, variously, a stent graft or a removable catheter balloon.

In another aspect, the present invention relates to a system for treating a patient that includes an endoprosthesis and a formulation adapted to form a polymer foam when exposed to a bodily fluid. The formulation is configured to sink in blood. The formulation, in some cases, sinks to the bottom of the aneurysm and forms a foam that expands upward to fill a volume of the aneurysm. In certain cases, the system also includes a catheter with a tip that can be placed within the aneurysm and which supplies the formulation to the aneurysm and/or removes blood that is displaced by the expansion of the foam. The catheter is, variously, sized to fit through the inferior mesenteric artery, through a fenestration within the endoprosthesis, or through a space between the endoprosthesis and the wall of a blood vessel fluidly connected to the aneurysm. The catheter may also include a retractable shield that inhibits the migration of the foam from the top to the bottom of the aneurysm, and the endoprosthesis may be, variously, a stent graft or a removable catheter balloon.

In another aspect, the present invention relates to a system that includes an endoprosthesis specifically configured to span an abdominal aortic aneurysm, a formulation that forms a polymer foam within the aneurysm, and a delivery catheter insertable through any of the inferior mesenteric artery, the lumbar artery, a fenestration in the endoprosthesis, and a space between the endoprosthesis and a blood vessel adjoining the aneurysm. The formulation is configured to migrate away from the catheter when it is delivered into the aneurysm, and then to form a foam that expands back towards the catheter.

In another aspect, the present invention relates to an in situ foaming formulation which forms a top-down foam. The formulation is, variously, entrained with a buoyant gas or comprises a low-density material so that it floats in a bodily fluid such as blood.

In another aspect the present invention relates to an in situ foaming formulation which forms a bottom-up foam which is more dense than a bodily fluid such as blood and thus sinks to the bottom of a cavity filled with such fluid.

In yet another aspect, the present invention relates to a catheter for delivering an in situ foaming formulation which includes a distal tip and a lumen. In various embodiments, the catheter includes an outer sheath catheter and an inner delivery catheter slidably and/or rotatably disposed within the outer sheath catheter. The catheter optionally includes one or more of a valve, a side aperture, a hydrophobic coating and a foam cutting member.

And in still another aspect, the present invention relates to a method of treating a patient by providing, to an aneurysm, an endoprosthesis and then delivering, to a space defined by an outer surface of the endoprosthesis and the inner surface of the aneurysm, an in situ foaming formulation, thereby filling the space with a polymer foam. The method optionally includes occluding at least one of an inferior mesenteric artery and a lumbar artery, providing the in situ foaming formulation with a catheter introduced into the space via the lumbar or inferior mesenteric arteries or via a fenestration in the endoprosthesis or via a space between the endoprosthesis and a blood vessel adjoining the aneurysm. The method also optionally includes removing the endoprosthesis after forming the foam.

These aspects are described more fully below.

DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1 shows the conventional placement of a stent-graft within an abdominal aortic aneurysm.

FIG. 2A-D includes several illustrations of an exemplary top-down foaming system. Prepolymer formulation floats to the top of the cavity due to entrained air and expands downward as foam, displacing fluid out the bottom, collateral vessels.

FIG. 3 shows a prototype of a catheter with a shield mechanism.

FIG. 4A-B shows illustrations of a laboratory model of aneurysm treated with a bottom-up foaming system. Prepolymer is injected into the top of an open fluid filled 10 cc syringe. The prepolymer sinks to the bottom to form a foam (arrow) but does not travel down the open 2 mm luer, simulating a lumbar artery.

Figure 7A:
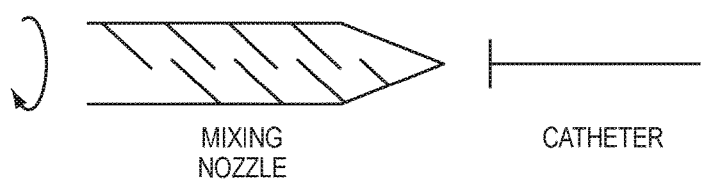
Figure 7B:
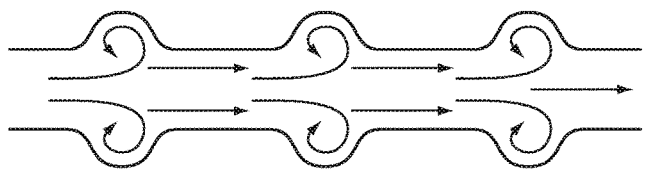

FIG. 7A-B shows two exemplary static mixing nozzle designs.

Figure 8A:
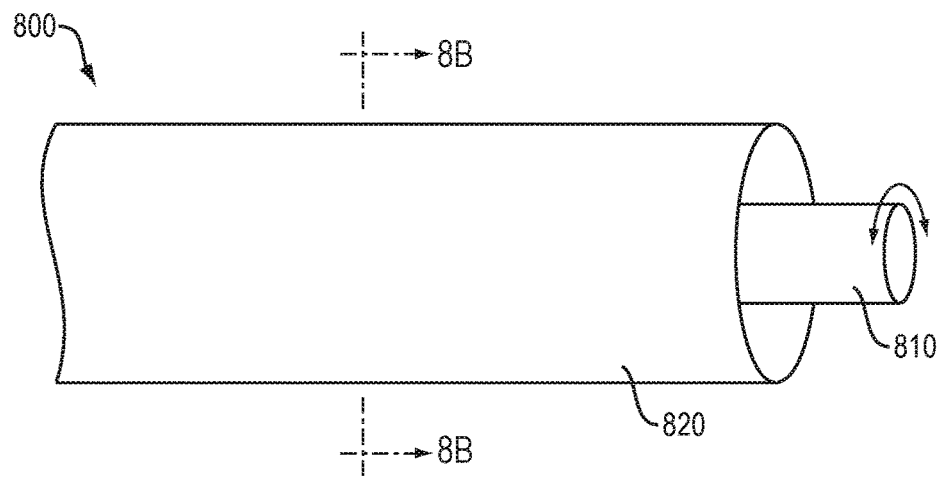
Figure 8B:
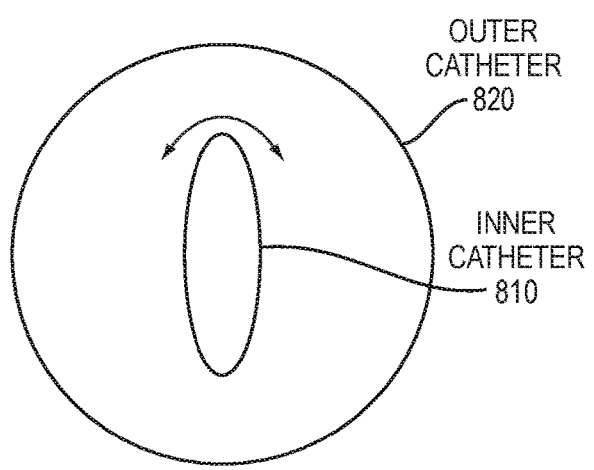

FIG. 8A-B shows an exemplary concentric dual lumen foam delivery catheter.

Figure 9A:
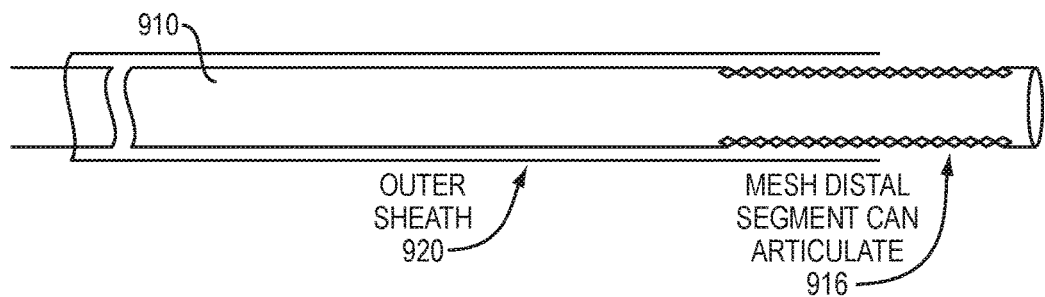
Figure 9B:
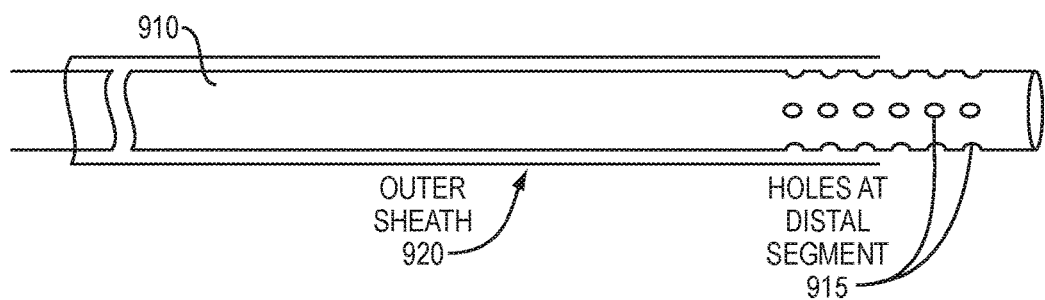

FIG. 9A-B shows an exemplary concentric dual lumen foam delivery catheter.

Figure 10A:
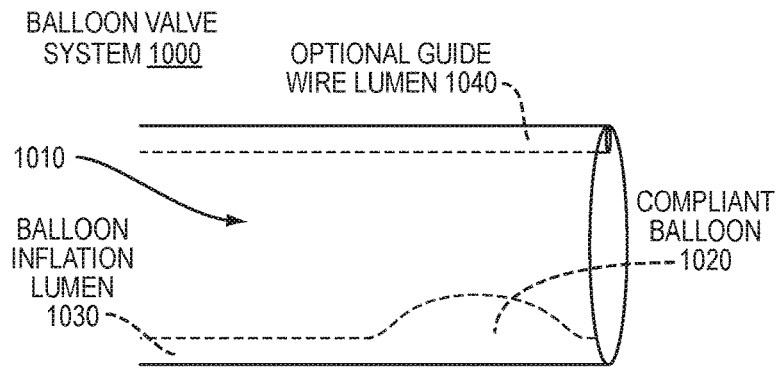
Figure 10B:
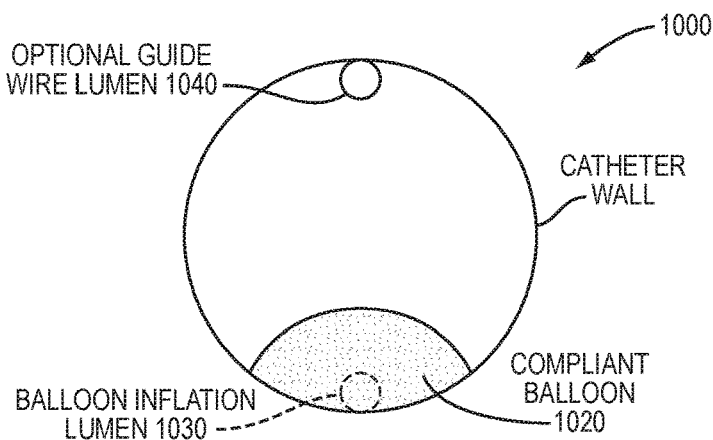
Figure 10C:
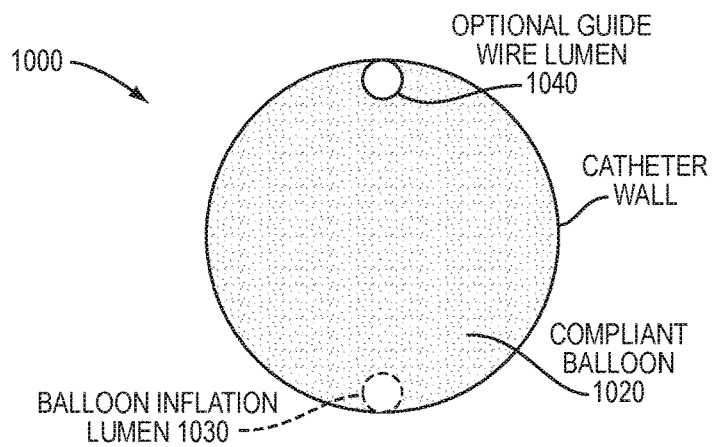

FIG. 10A-C shows different views of an exemplary balloon valve for a delivery catheter.

Figure 11A:
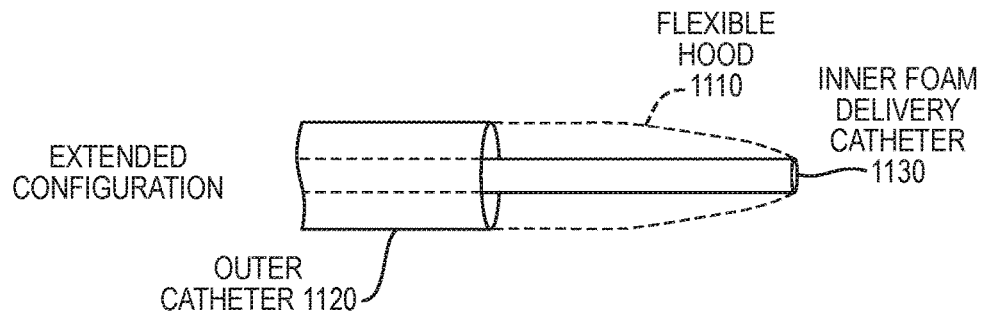
Figure 11B:
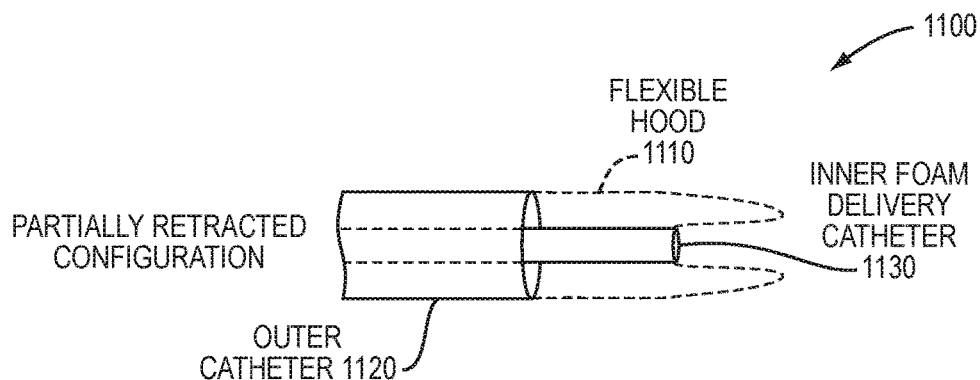
Figure 11C:
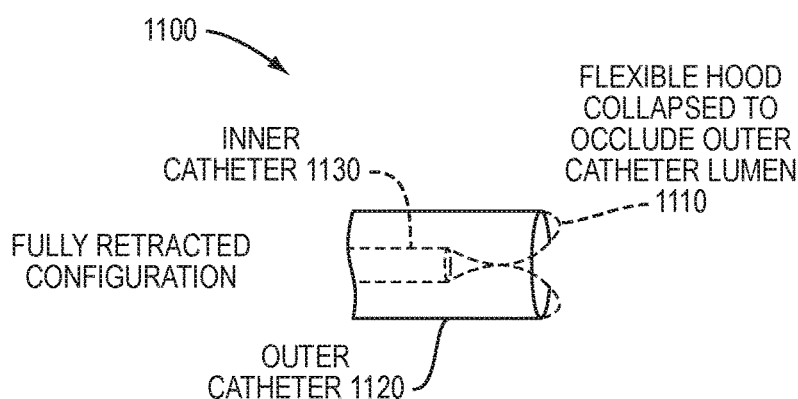

FIG. 11A-C shows different views of an exemplary retractable hood system for a delivery catheter.

Figure 12:
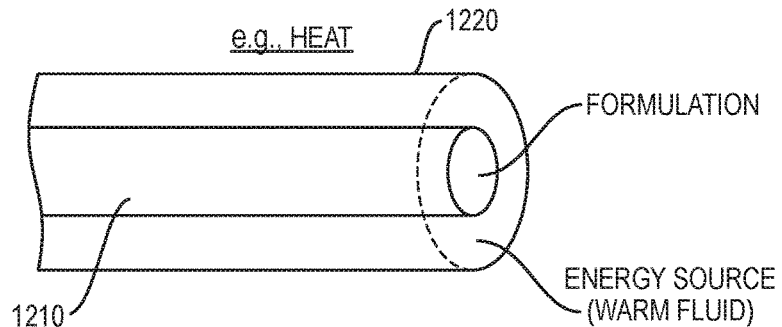

FIG. 12 shows an exemplary coaxial dual lumen catheter for delivering a temperature- or energy-sensitive in situ foaming formulation.

Figure 13:
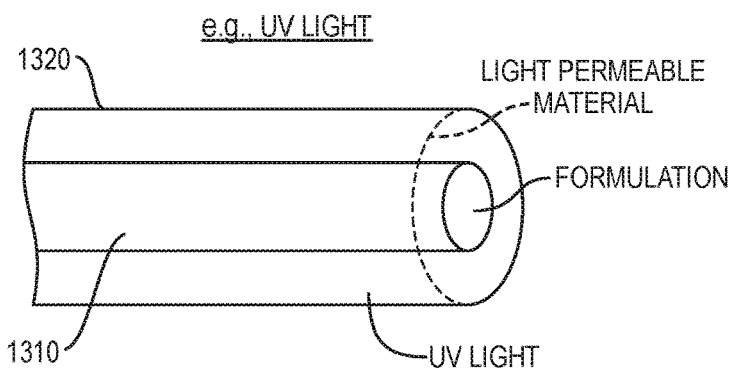

FIG. 13 shows an exemplary coaxial dual lumen catheter for delivering a light-sensitive in situ foaming formulation.

Figure 14:
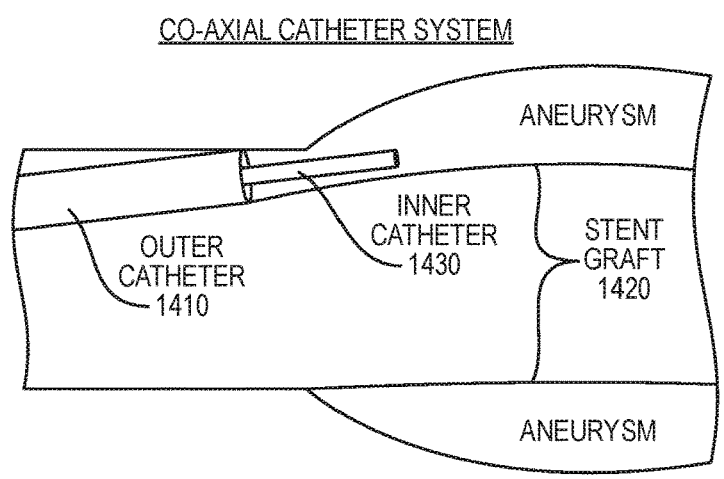

FIG. 14 shows a delivery catheter insertable through a space between a stent graft and a blood vessel adjoining an aneurysm.

Figure 15A:
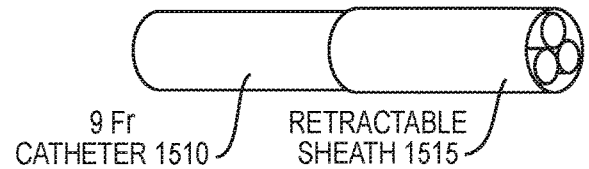
Figure 15B:
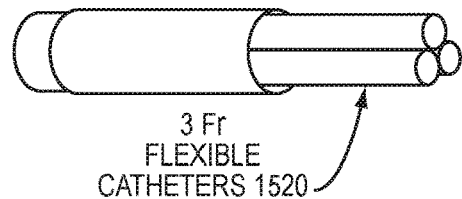
Figure 15C:
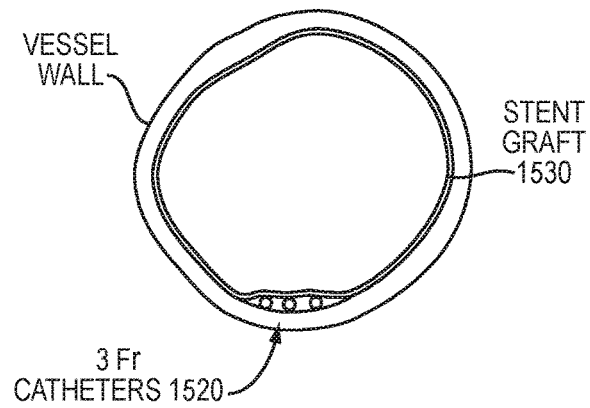

FIG. 15A-C shows multiple views of an exemplary split-lumen delivery catheter held together with a retractable sheath.

Figure 16:
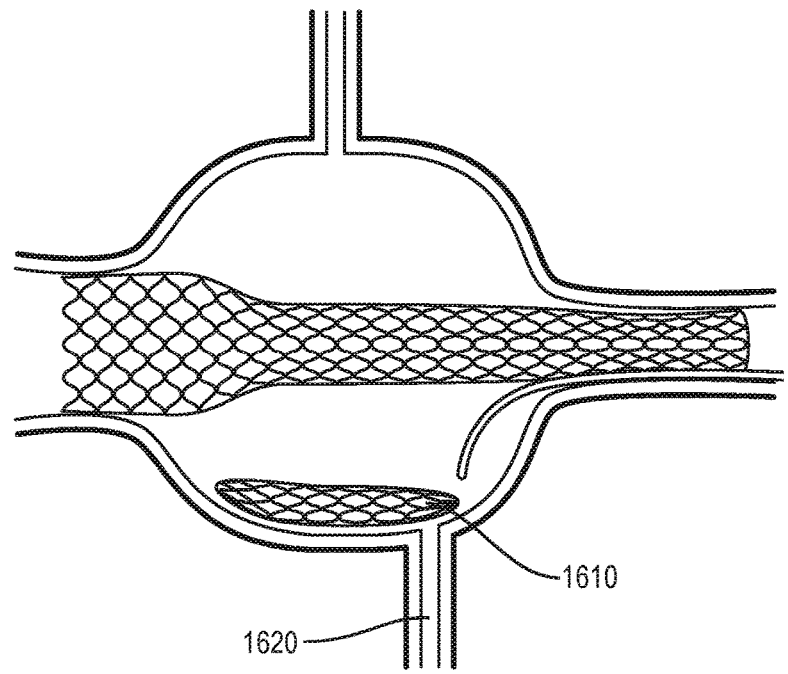

FIG. 16 shows a schematic view of the occlusion of a lumbar artery within an AAA according to certain embodiments of the present invention.

Figure 17:
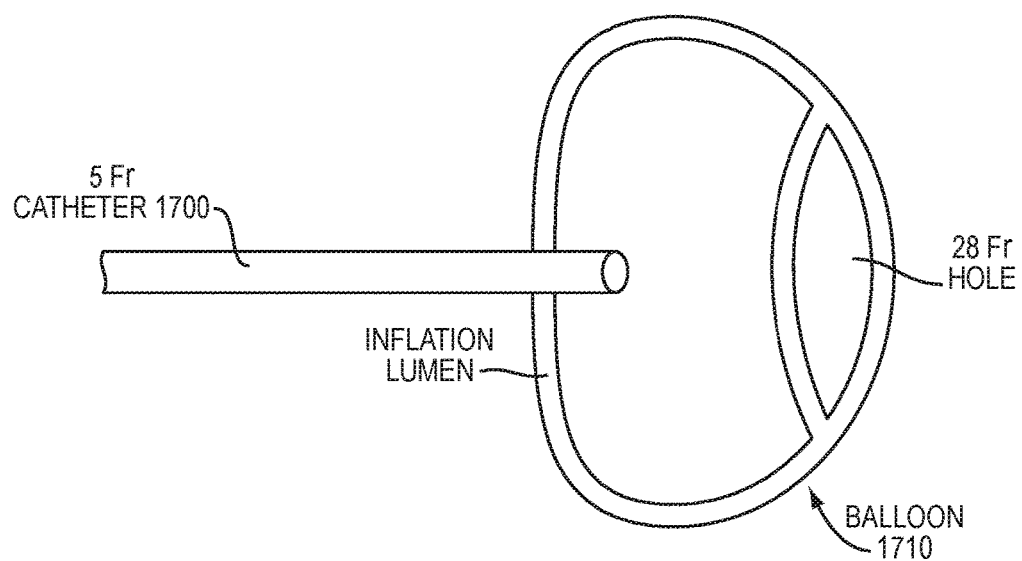

FIG. 17 shows a schematic view of an exemplary delivery catheter having an expandable balloon tip.

Figure 18A:
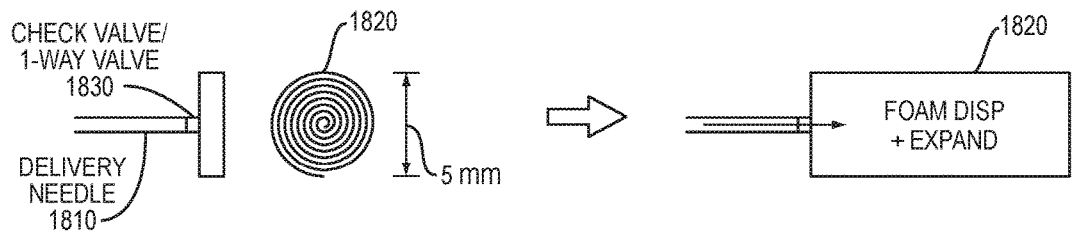
Figure 18B:
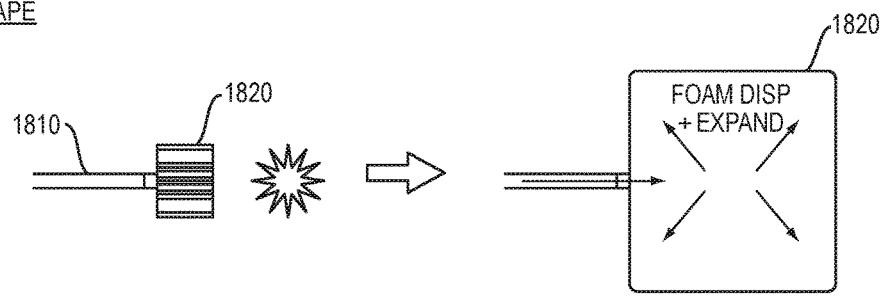
Figure 18C:
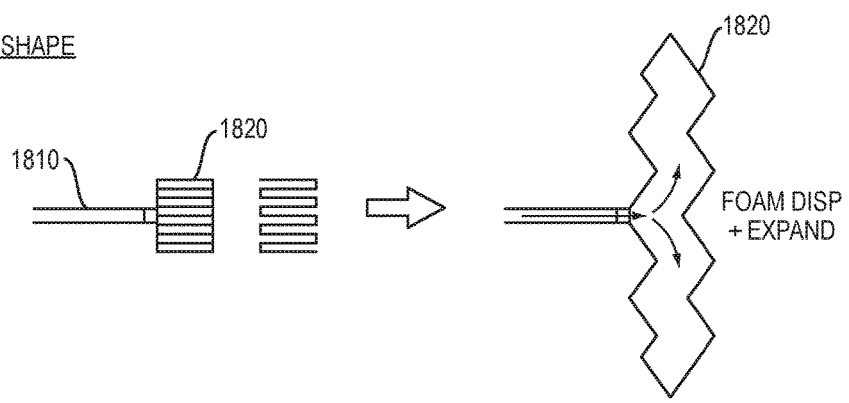

FIG. 18A-C show schematic views of exemplary delivery catheters having expandable tips and/or bags.

Figure 19:
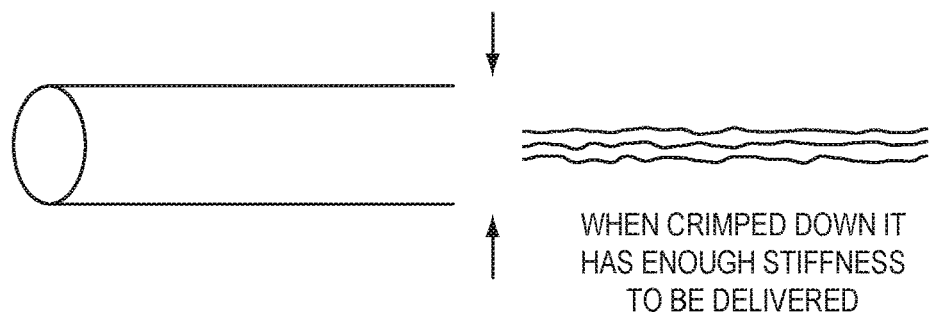

FIG. 19 shows an exemplary crimpable tube useful in various embodiments of the invention.

Figure 20:
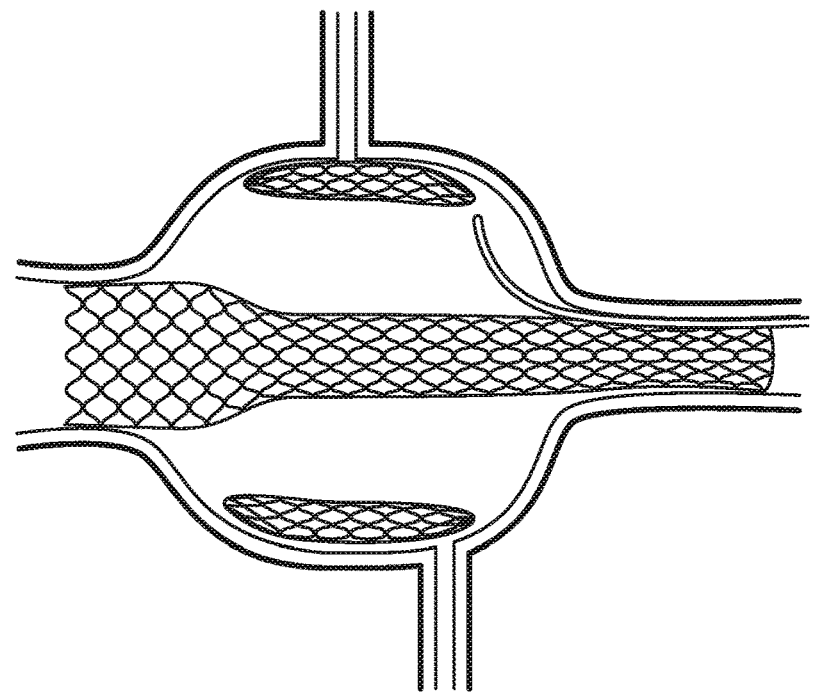

FIG. 20 depicts the occlusion of the IMA and the lumbar artery within an AAA according to certain embodiments of the invention.

FIG. 21 depicts a delivery catheter having a side port for delivering an in situ foaming formulation.

FIG. 22A-C depicts a guidewire compatible delivery catheter that includes a check valve and side apertures for delivery of an in situ foaming formulation.

Figure 23:
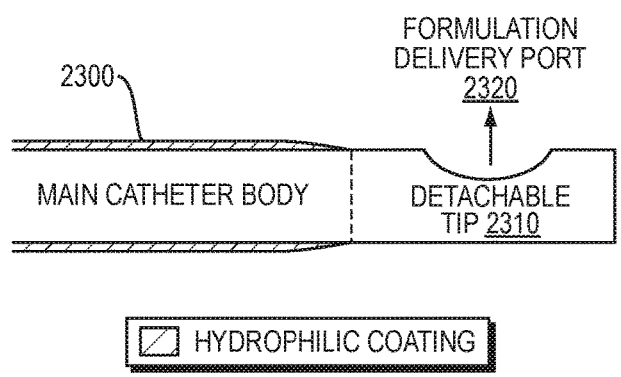

FIG. 23 depicts a delivery catheter with a detachable tip.

Figure 24:
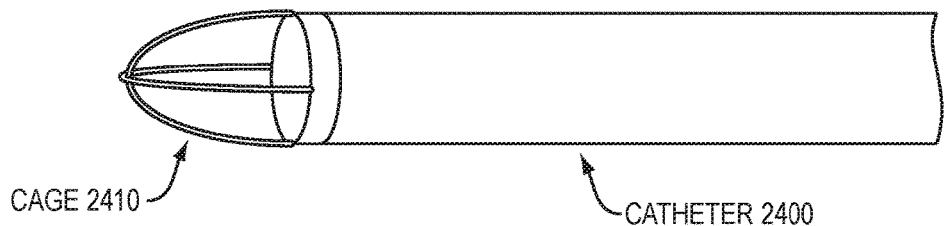

FIG. 24 depicts a delivery catheter with a detachable tip.

FIG. 25A-B depicts a delivery catheter with a foam cutting member.

FIG. 26 depicts a delivery catheter with a check valve disposed at its distal tip.

Figure 27C:
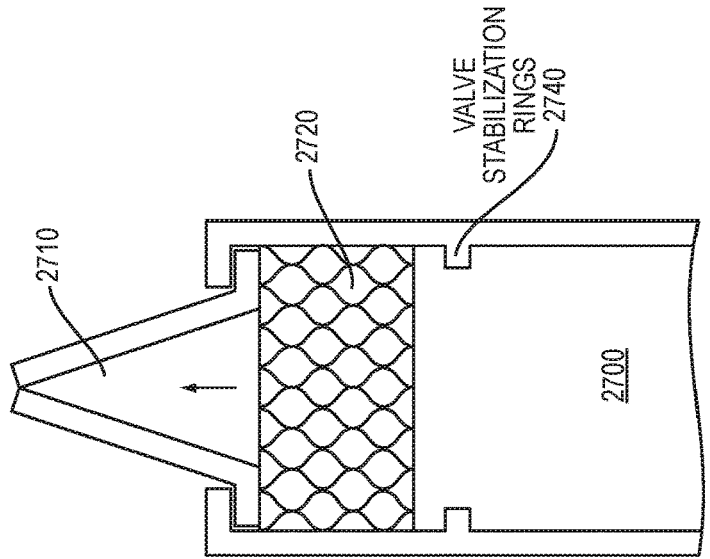
Figure 27B:
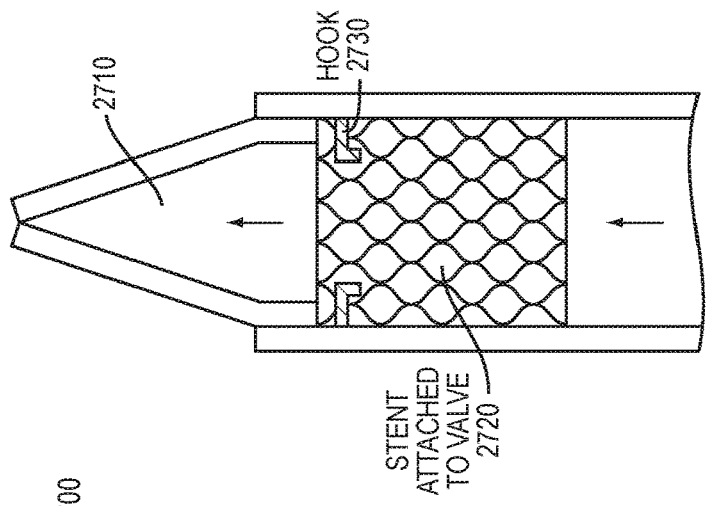
Figure 27A:
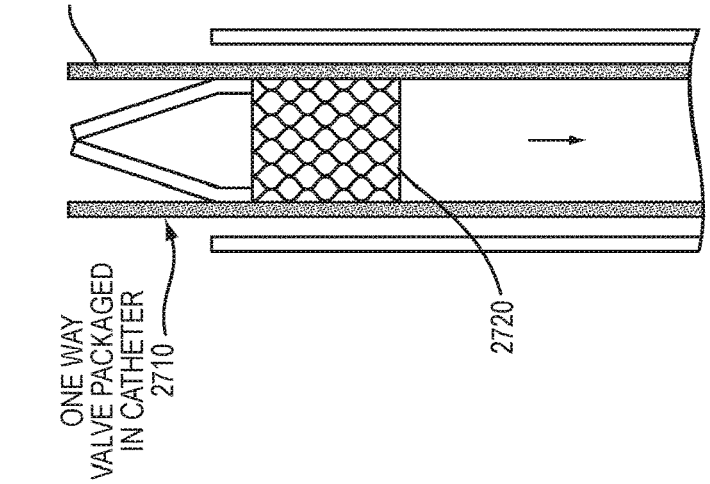

FIG. 27A-C depicts an exemplary valved delivery catheter according to certain embodiments of the invention.

FIG. 28A-B depicts an alternative design for a valved delivery catheter according to certain embodiments of the invention.

FIG. 29A-C depicts a delivery catheter utilizing a ball valve.

Figure 30A:
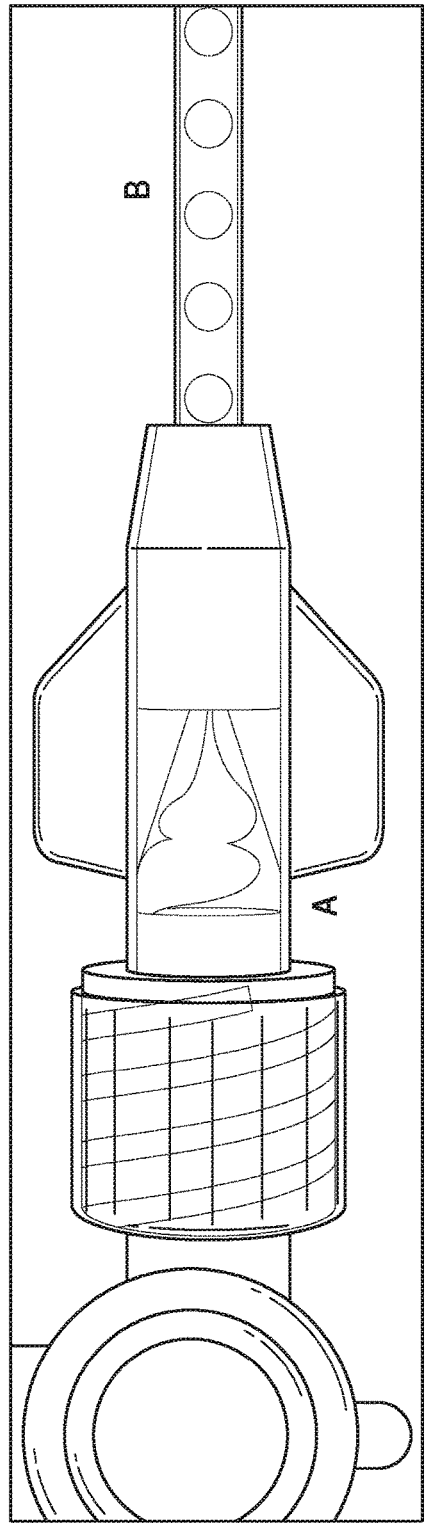
Figure 30B:
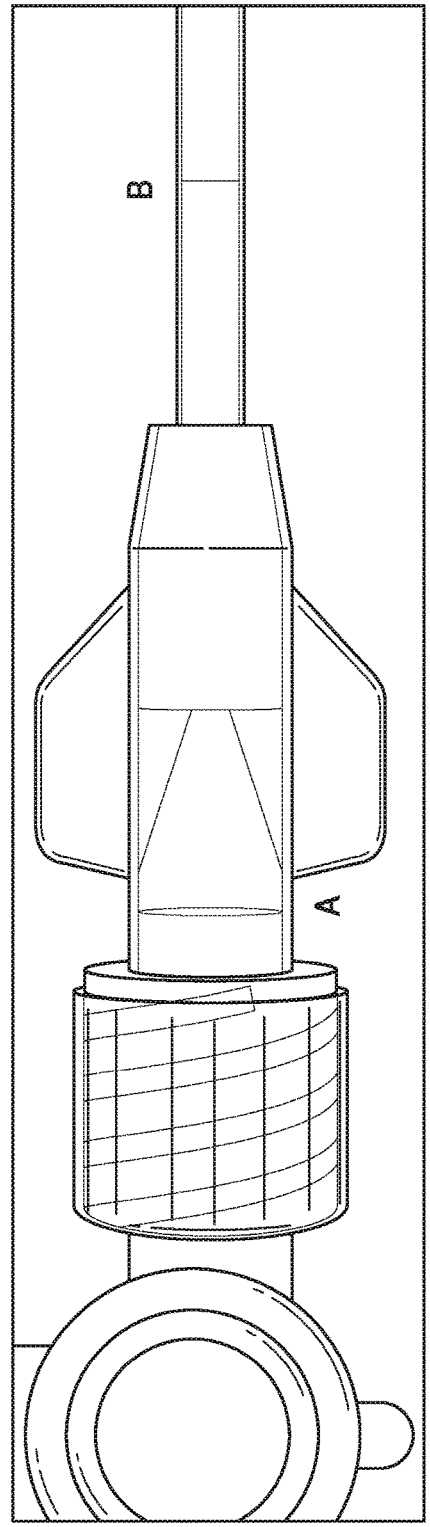

FIG. 30A-B depicts the behavior of fluid junctions between viscous in situ foaming formulations and non-viscous flush solutions at high (top) and low (bottom) flow rates.

Figure 31:
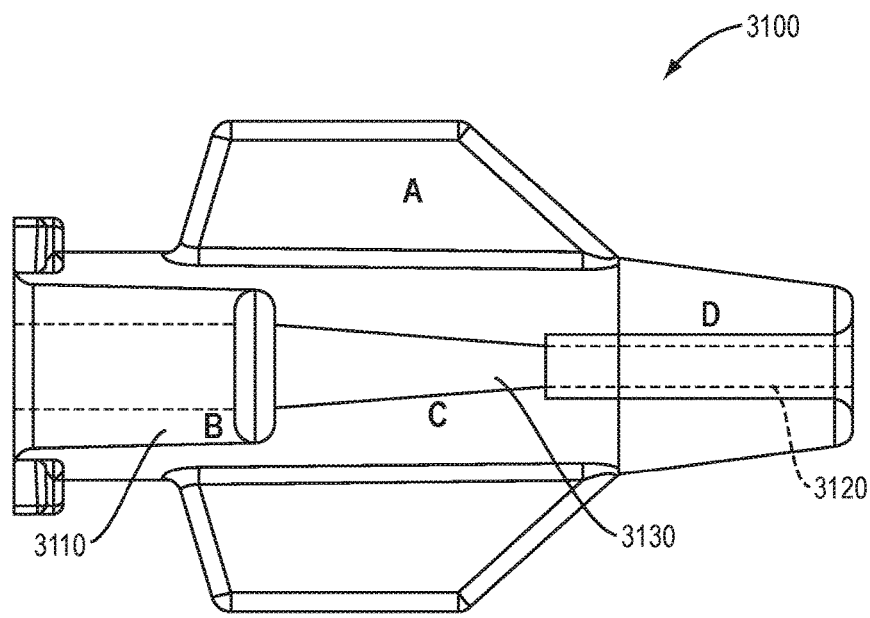

FIG. 31 depicts an exemplary fluid connector according to certain embodiments of the invention.

Figure 32:
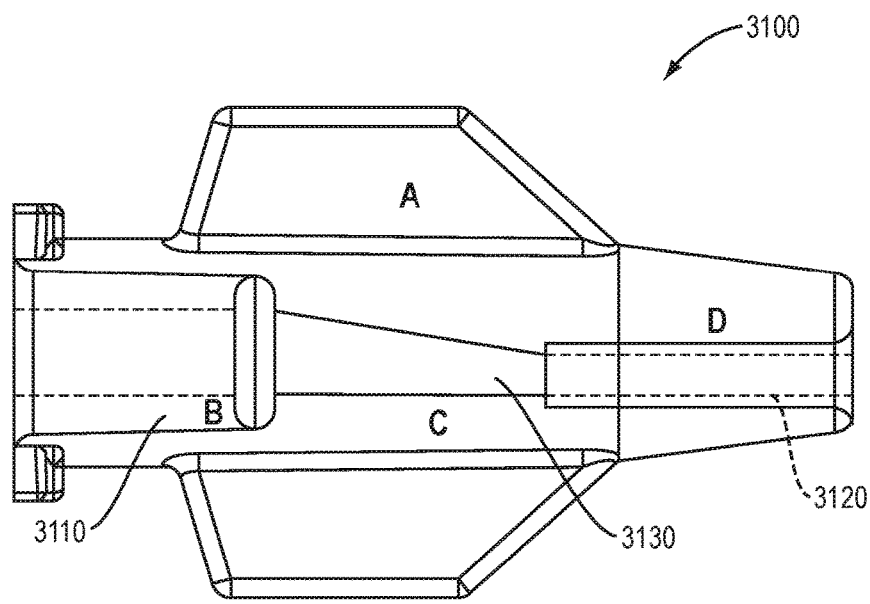

FIG. 32 depicts an exemplary fluid connector according to certain embodiments of the invention.

DETAILED DESCRIPTION OF THE PREFERRED EMBODIMENTS

Systems, methods and kits related to the treatment of aneurysms using in situ forming polymer foams are generally described. As will be recognized by those skilled in the art, although the present invention is described with specific reference to the use of in situ forming foams within aneurysm sacs, the foams of the present invention may be applied to any body cavities such as abdominal, pelvic, and cardio thoracic cavities, and placed in contact with, for example, tissue, injured tissue, internal organs, etc. As used herein, "aneurysm sac" refers to the sac formed by the localized dilation in a blood vessel at an aneurysm site.

Polymer foams and foaming formulations used in various embodiments of the invention are described in U.S. application Ser. No. 13/532,013 by Sharma, et al. entitled "In situ Forming Foams for Treatment of Aneurysms" filed Jun. 25, 2012, which is incorporated herein for all purposes. The polymer foams used in various embodiments of the present invention are formed in situ. That is, the foams are formed by the reaction of polymer(s) in an aqueous environment simultaneously with, or shortly after, delivery to an aneurysm sac. This is in contrast to pre-formed foams, which are formed prior to the time that they are delivered into the body. The foamed polymers of the present invention may be capable of exerting a pressure on an internal surface of an aneurysm sac and thus prevent or limiting movement of a bodily fluid (e.g., blood, etc.) and/or prevent or limit endoleaks as previously described. Such in situ forming foams preferably expand to fill the aneurysm sac volume, resulting in conformal contact with the aneurysm walls and penetration into blood vessels and other lumens opening into the sac. The location of such vessels is not always obvious with standard imaging technique, such that the ability to seal such vessels with the foams and methods of the present invention without requiring visualization is a unique advantage of the present invention. Also, the foams are formed by the reaction of polymers in situ to yield gas generation and expansion, which allows for the use of minimal polymer materials and allows the resulting foam to push through fluid, including actively flowing blood, to provide conformal contact with surrounding tissue. Finally, an additional advantage of the present invention is the added structure and anchoring sites within collateral vessels following formation of a fully formed foam. Such anchoring sites may provide for the anchoring or stabilizing of an implanted graft or stent-graft, thus preventing migration thereof. These and other factors are important distinctions and advantages of in situ forming foams over systems and methods that make use of pre-formed foams.

Figure 1:
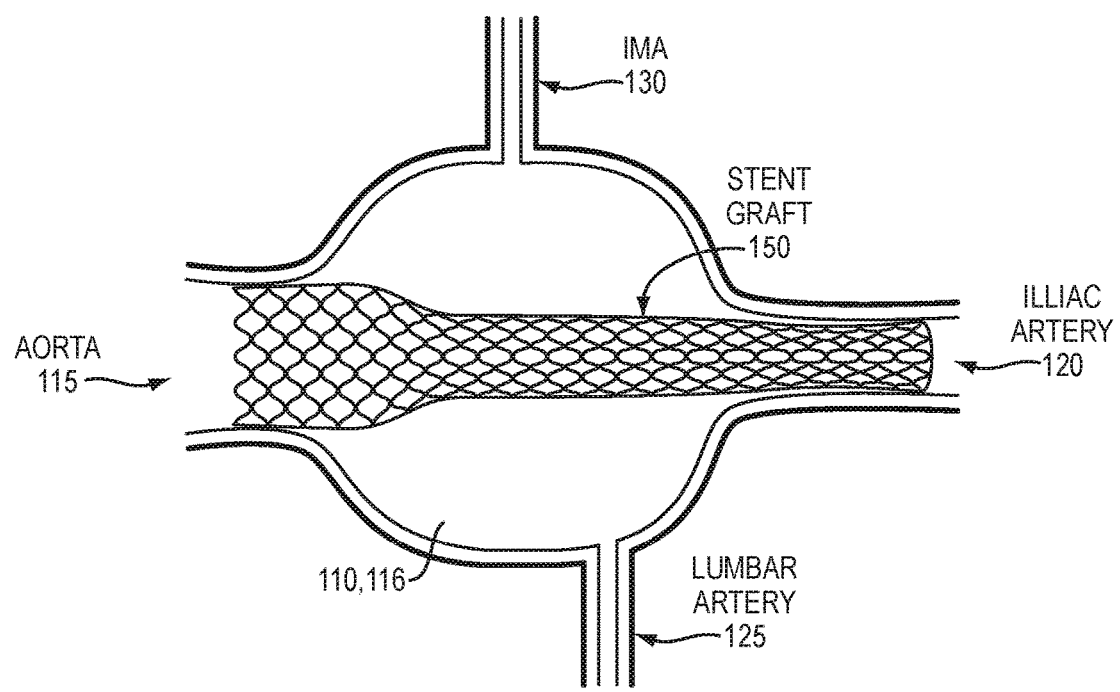
Figure 2A:
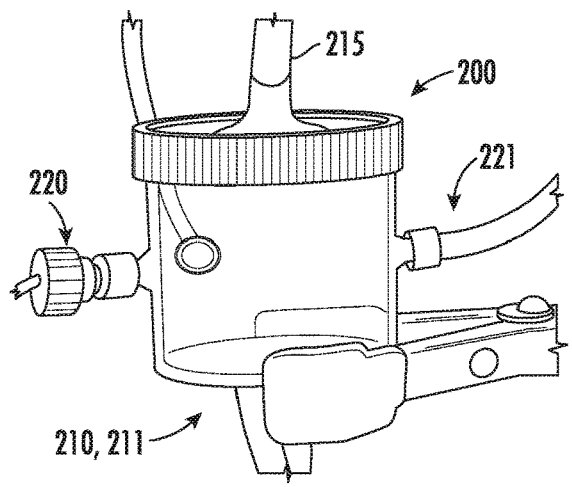
Figure 2B:
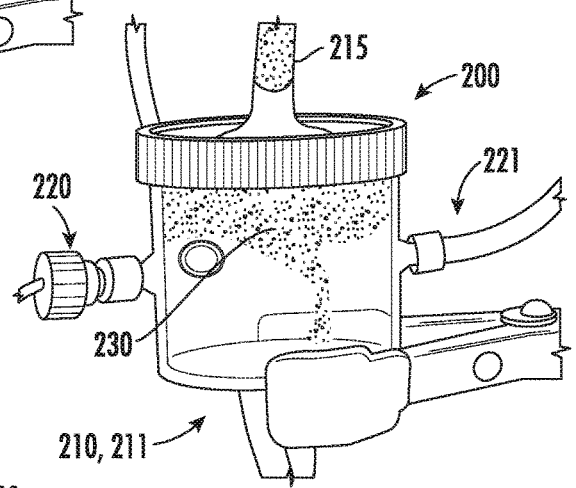
Figure 2C:
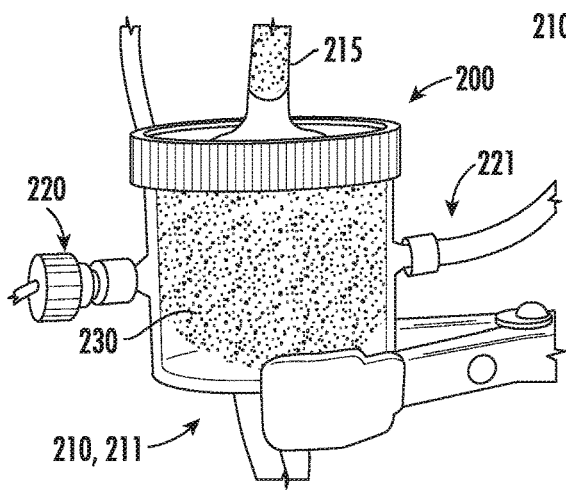
Figure 2D:
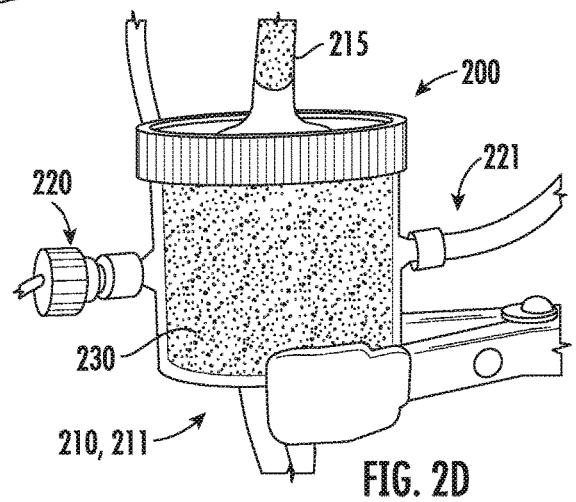

The systems and methods of the invention are advantageously used in EVAR procedures to fill the aneurysm space and neighboring tributaries surrounding a stent graft as completely as possible with foam, including occluding possible routes of fluid entry via collateral vessels, the dorsally-located lumbar arteries and the ventrally-located inferior mesenteric artery (IMA). FIG. 1 depicts a lateral view of an abdominal aortic aneurysm (AAA) and its collateral vessels. The stent graft bridges the aorta and iliac arteries 115, 120, excluding the aneurysmal sac from aortic flow. Occlusion of the lumbar artery 125 and the IMA 130 prevents so-called type II endoleaks in which the aneurysm continues to expand with fluid supplied via these vessels.

Although the present invention is described with specific reference to aneurysms in the aorta and iliac arteries, it should be appreciated that the devices, systems and methods of the present invention are applicable to aneurysms throughout the vasculature. Certain aspects of the present invention are applicable to vascular embolization more generally, for instance to obstruct blood vessels providing blood flow to tumor tissue, or to tissue that will be resected. Additionally, some aspects of the invention are useful in the occlusion of fluid-filled body lumens more generally.

Top-Down and Bottom-Up Foaming Formulations

As used herein, the terms "top" and "bottom" refer to the gravitational top and bottom of a cavity into which the prepolymer formulation is introduced. For example, the top refers to the point at which a buoyant material (e.g. air) would collect within a water- or blood-filled cavity and the bottom refers to the location where a dense solid would collect. By way of further example, for a patient undergoing EVAR lying supine on an operating table, the top would refer to the ventral or anterior wall of the aneurysm and bottom to the dorsal or posterior wall.

For the purposes of this disclosure, the terms "formulation", "prepolymer", and "prepolymer formulation" are used interchangeably to designate a polymer-based system or material capable of further reaction in the aneurysm or fluid-filled space. These terms can refer to a single prepolymer material, or a prepolymer material blended with other additives (e.g., catalysts, surfactants, solvents, diluents, crosslinkers, chain extenders, blowing agents) to create a prepolymer formulation. Upon reaction, cross-linking, or curing, the formulation will form and expand into a foam.

Foams and formulations of the invention, when used to treat or prevent endoleaks, are preferably disposed within an aneurysm sac to fill a space defined by the outer surface of an endoprosthesis such as a stent graft and the inner surface of the aneurysm sac. In use, the foam is formed during or after a procedure to place a stent graft within the aneurysm; after the stent graft has been positioned, an in situ foaming formulation according to an embodiment is disposed within the aneurysm, preferably resulting in the formation of a substantially contiguous foam wall between the stent graft and the inner wall of the aneurysm, further stabilizing the aneurysm. The foam most preferably displaces substantially all of the pooled blood within the aneurysm, (e.g., inferior mesenteric artery and lumbar artery branch point from the aneurysm, and stent-graft interfaces with the aneurysm wall) and does not necessarily fill the full volume of the aneurysm sac outside of the stent graft.

Two exemplary embodiments of the invention are a top-down system and a bottom-up system, as described below.

Top-Down System

Top-down foaming systems according to various embodiments of the invention utilize in situ foaming formulations which are more buoyant than the bodily fluid or fluids occupying a body lumen or cavity to be filled. The formulations are typically delivered via catheters and are preferably delivered so that the expanding foam generated by the formulation evacuates fluid from the body lumen or cavity being filled. In preferred embodiments the formulation is delivered by a catheter with a distal tip positioned at the bottom of the lumen or cavity. Where the system is used to treat AAA, the catheter is positioned within the aneurysm 110 near the lumbar artery 125. As the formulation is expelled from the catheter into the fluid-filled lumen or cavity, it rises to the top of the lumen or cavity due to entrained air or due to the density of the formulation itself. The formulation subsequently generates a polymer foam which expands from the top of the lumen or cavity to bottom, displacing the resident fluid in the lumen or cavity down toward the bottom of the lumen or cavity such that the fluid is forced to exit the lumen or cavity via the vessels at the bottom of the cavity or lumen (e.g., via the lumbar arteries).

The top-down system has a particular advantage for the treatment of aneurysms such as AAA in which a catheter cannot be delivered to the top of the lumen. Another general advantage of positioning the catheter at the bottom of the chamber is that the delivery catheter will remain open until substantially all of the body lumen or cavity has been filled in with foam.

The top-down concept is illustrated in FIG. 2, in which a plastic cup 200 is used as an aneurysm model with two lumbar arteries 210, 211 (bottom) and one IMA 215 (top). Additionally, the model contains two side apertures 220, 221 to represent possible venting through additional catheters in the system. The tubing is adjusted to a height pressurizing the vessel at 70 mmHg, consistent with the pressure of an excluded aneurysm sac. A prepolymer formulation is injected via the delivery catheter (PEBAX, 5 Fr), and it initially rises (FIG. 2A) to the top of the aneurysm. Subsequently, the foam 230 occludes the IMA 215 and pools at the top of aneurysm model 200 (FIG. 2B). The foam 230 then expands downward (FIG. 2C), forcing fluid through the side apertures/lumbar arteries 220, 221 until the space within the aneurysm/cup 200 is filled (FIG. 2D). This example demonstrates top-down directional foaming that expels the blood from the aneurysm in a controlled fashion.

Foam Properties for a Top-Down System

Prepolymer formulations used in the top-down foaming system may contain additives or may be otherwise specially formulated to promote foaming from the top downwards. This includes methods of imparting buoyancy to the prepolymer formulation (i.e., creating a formulation that has a lower density than blood).

One method that may be employed to impart buoyancy to the prepolymer formulation is the entrainment therein of gas, such as carbon dioxide, nitrogen, oxygen, or mixtures thereof. Entrainment of gas into the prepolymer formulation may be achieved, for example, by whipping the formulation with an impeller mixer prior to injection, repeated transfer between multiple syringes connected by a stopcock, manual shaking, vortexing, or other suitable means. Additionally, gas may be delivered as a separate component via a specialized catheter (e.g., a concentric catheter in which gas is delivered in the outer space and mixed at point of deployment, as described below). In the case of multiple syringe transfer, the gas may be pre-packaged into the head space of one or more of the syringes or its own individual syringe. Gas entrainment causes the injected prepolymer formulation to float to the top of the lumen or cavity prior to or during curing or foaming, allowing the curing or foaming to proceed in a top-down fashion. Alternatively, gas may be entrained by supersaturating the mixture with gas and delivering the formulation under pressure.

Entrainment of gas to achieve buoyancy can also be achieved by the addition of a blowing agent to the foaming formulation, or through the pre-reaction of polyol and isocyanate groups on the prepolymer and cross-linker used to generate a polyurethane foam. This could be achieved by including a small amount of water in the formula, in a separate syringe mixed prior to injection, allowing reaction within the delivery catheter, or delivering a stream of water along with the prepolymer stream.

Prepolymer formulation buoyancy is also affected by adjusting the density of the prepolymer formulation or by using additives such that the prepolymer formulation (aerated or unaerated) is less dense than blood (roughly 1.05 g/ml). This is done in some embodiments via inclusion of low-density prepolymers such as TDI-terminated polypropylene glycol (Sigma Aldrich prod no. 433497, MW 2300 g/mol, 1.05 g/ml), low-density diluents such as acetone (0.786 g/ml), 2-butanone (0.8 g/ml), or ethyl formate (0.92 g/ml), or using other formula components with sufficiently low density to bring the overall formula density into the desired range. Other formula components could be suspended particles, fibers, or other materials with sufficiently low density.

An example of a suitable prepolymer formulation that may be used in the present invention comprises the following mixture, with actual mass amounts used for the aneurysm experiment in parentheses: 80 parts Lupranate 5020 prepolymer (18.06 grams), 20 parts Nanopol700 prepolymer (0.2 g), 20 parts dimethylsulfoxide (0.2 g), 1 part bis-(2-dimethylaminopropyl) ether catalyst (225 mg), 3 parts DABCO DC5098 surfactant (644.1 mg). In total, 15 ml of this formulation was injected and the total aneurysm volume was 120 ml.

Foam Delivery for Top-Down System

A number of mechanical methods are applicable to the present invention in addition to the chemical methods described above. Exemplary foam delivery catheters and systems are described below.

Delivery catheter with a curved tip. A delivery catheter with a curved tip is, in some embodiments, placed into the fluid-filled lumen or cavity such that the tip of the catheter navigates around the vascular graft to deliver prepolymer formulation ventral to the graft. Here, the tip of the delivery catheter is straight when placed over a guidewire and becomes curved when the guidewire is released. The tip of the delivery catheter optionally contains a radiopaque marker band for visualization and placement.

Delivery Catheter with a Multi-Prong, Curved Tip.

According to some embodiments of the present invention, a delivery catheter splits or forks at or near its tip to yield two or more separate, curved exit lumens that are placed into the lumen or cavity such that each of the prongs laterally circumvents the vascular graft. The curvature of the tips causes the distal exit ports to land or seat ventral to the graft where the two or more streams of prepolymer will be delivered.

Venting Catheter.

A simple aspiration, or venting, catheter may also be introduced into the bottom of the lumen or cavity to provide an outlet for displaced blood. In one such embodiment, a microcatheter with a diameter less than 5 French is introduced in the iliac artery contralateral to the delivery catheter. In another embodiment, the delivery catheter contains multiple lumens, one of which is reserved for the purpose of venting. The aspiration rate is preferably approximately equal to the delivery rate of the prepolymer formulation, so that the volume within the sac remains constant.

In other examples, percutaneous embolization of the IMA is achieved through catheterization of arteries such as, but not limited to, the Superior Mesenteric Artery and access to the IMA through the Arch of Riolan or the Superior Marginal Artery. In these embodiments, stainless steel embolic coils are optionally placed into the IMA to seal it of from systemic circulation. The aneurysm sac is then filled with the top-down foaming formulation, which displaces blood into the lumbar arteries and/or into an aspiration catheter positioned at the bottom of the aneurysm sac.

In another example, the IMA is blocked with the formed foam material. Features included in the delivery system assist the prepolymer formulation stream into assuming a form factor during curing or cross-linking suited to block the IMA without unacceptable migration of foam into downstream vasculature. This is achieved in several ways as described below.

Shield Catheter.

Figure 3:
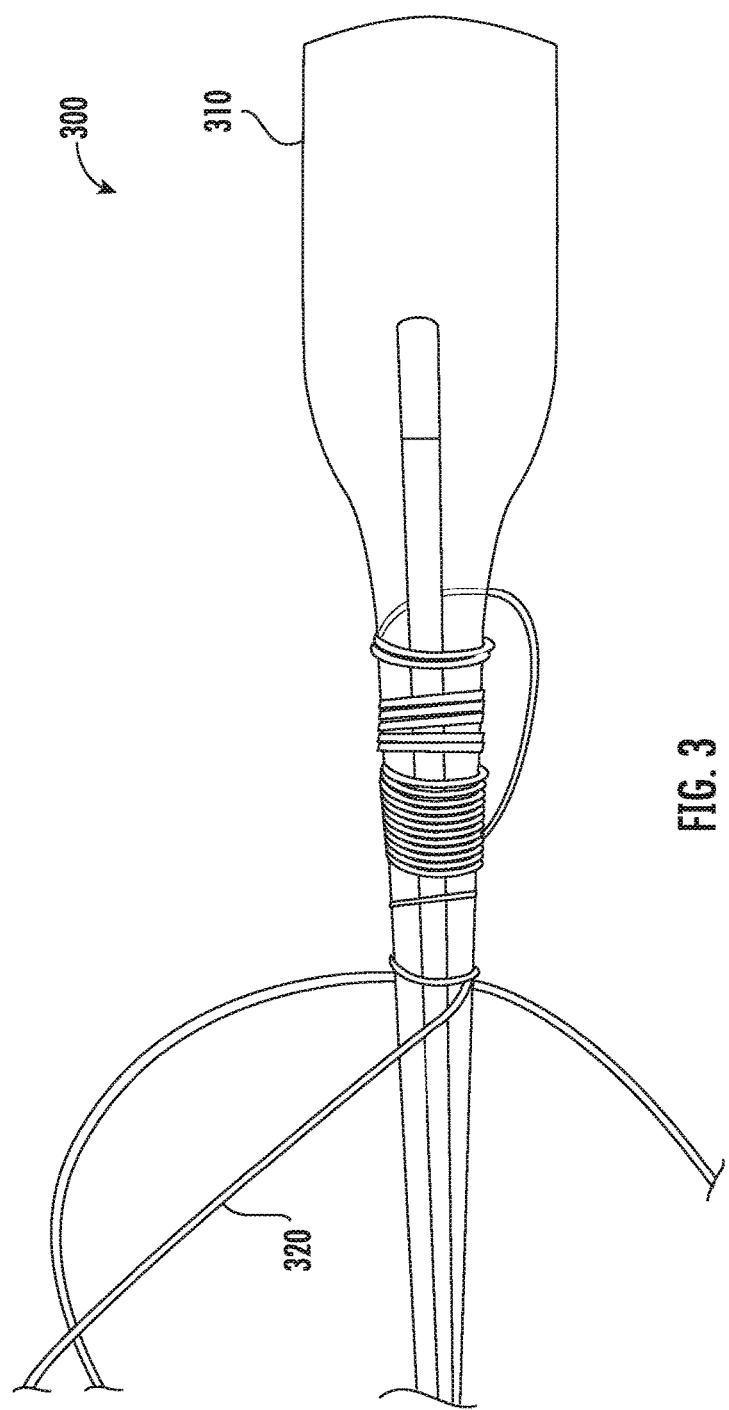

An exemplary e catheter 300 according to certain embodiments of the invention includes a broad, flat or slightly curved "shield" 310 which is sufficiently flexible or elastic to be rolled or contained within the delivery catheter and then released to catch or collect prepolymer formulation dispensed from the catheter tip, as shown in FIG. 3. The buoyant prepolymer formulation is delivered slowly (preferably less than 5 ml/min.) until a sufficiently large globular mass of prepolymer formulation has accumulated. The shield is then retracted by retracting a suture 320 connected to the shield 310, allowing the foaming formulation to float upward. The use of a shield 310 advantageously permits the deployment of a substantially uniform bolus of formulation into an aneurysm, which in turn contributes to the formation of a unified foam therewithin. A unified foam formed in this manner advantageously resists breakage to pieces which may migrate undesirably into the adjacent vasculature.

Slit or Bevel Catheter.

A delivery catheter with a slit running parallel to the direction of the lumen may be used to deliver prepolymer formulation in a stream wide enough to prevent prepolymer formulation from migrating into the downstream vasculature (i.e., prepolymer is cross-linked or cured and a foam is formed in pieces too large to embolize down the lumbars).

Rotating Catheter.

A delivery catheter with an inner rotating shaft may be used to cause the prepolymer formulation stream leaving the catheter tip to wind around the catheter shaft and form a globular mass. When the mass becomes sufficiently large, it will break away due to buoyancy forces, and float to the top of the sac to block the IMA.

Aspiration Catheter.

A separate aspiration catheter with its tip placed at the bottom of the sac may be used to withdraw blood at such a rate that flow from collateral vessels will be forced into the sac. This flow pattern is established just prior to the delivery of the prepolymer formulation. When prepolymer formulation is released at a sufficiently slow rate, the flow field created will prevent the prepolymer formulation stream from entering collateral vessels.

In other examples, mechanical features deployed from or as part of the delivery system are utilized to seal off the IMA. Two means of achieving this are described below.

A balloon, initially contained within a catheter and released within the lumen or cavity, is inflated with gas or a low density liquid (<1.05 g/ml) such that it floats or rises to the top of the lumen or cavity. The balloon should be sufficiently thin so as to obstruct only a very thin top layer of the sac and the IMA. The balloon can be biodegradable, dissolvable, or permanent.

Similarly, a buoyant sheet, delivered through a catheter, can be deployed and float or rise to the top of the lumen or cavity to provide a physical matrix onto which prepolymer adheres, or a physical matrix to which the prepolymer is impermeable, thus preventing unacceptable migration of foam into the IMA and downstream vasculature. The buoyant sheet could be porous or non-porous and permanent, dissolvable, or degradable.

Bottom-Up Foaming System

In some embodiments of the current invention, an in situ foaming formulation with a low buoyancy/high density is delivered into a fluid-filled body lumen or cavity to provide "bottom-up foaming." In these embodiments, the foam is preferably delivered at the top of the lumen or cavity, and sinks through the fluid to the bottom As described above, the formulation is, in various embodiments, delivered via catheter. Positioning the catheter at the top of the lumen or cavity in these embodiments is advantageous in that it does not require the prepolymer formulation to rise to the top of the cavity prior to crosslinking, curing, or foaming, yet still pushes out the resident fluid in a unidirectional fashion. This ensures that fluid is removed during foam rise, preventing pressure buildup and rupture. All lumbar vessels are preferably occluded, either by the foam, or alternative means as discussed below. In certain embodiments, a system for treating a patient according to the present invention includes multiple in situ foaming formulations which are deployed sequentially and/or simultaneously. The foams optionally have different characteristics including buoyancy, density and/or compliance of the resultant foams, or different foaming kinetics. For example, in some embodiments the system includes a first formulation adapted to form a conformal seal with a dorsal portion of the cavity or lumen, and a second formulation which generates a bottom-up foam layer on top of the foam formed by the first formulation. In other embodiments, the system utilizes a single formulation that can both seal the dorsal vessels and expand upward to fill the cavity.

Foam Properties for Bottom-Up System

In addition to the previously described properties and compositions of in situ forming foams for sealing endoleaks as described in U.S. application Ser. No. 13/532,013, which is incorporated herein for all purposes, prepolymers formulations used in the bottom-up foaming system may contain additives or may be otherwise specially formulated to prevent prepolymer formulation from entering the lumbar arteries.

For example, high viscosity may be imparted to the prepolymer formulation, as well as fast reaction kinetics to sufficiently crosslink or cure the prepolymer before transport to the delivery site can occur. Methods for increasing viscosity include using prepolymers of high molecular weight, increasing interactions between prepolymer chains (e.g., through hydrogen bonding), decreasing the diluent content, and other methods known to one skilled in the art. Methods for increasing the rate of reaction include increasing the amount of catalyst in the system, using multiple or more active catalysts, increasing the hydrophilicity of the system, increasing the functionality of the prepolymer, and other methods known to one skilled in the art. To prevent embolization, it is preferable to use prepolymers with functionality greater than 2.0 functional groups per molecules, more preferably greater than or equal to 3.0 functional groups per molecules, because, without wishing to be bound by theory, higher functionality polymers are more likely to be bound into the foam matrix rather than breaking off to form emboli down a vessel.

Figures 4A, 4B:
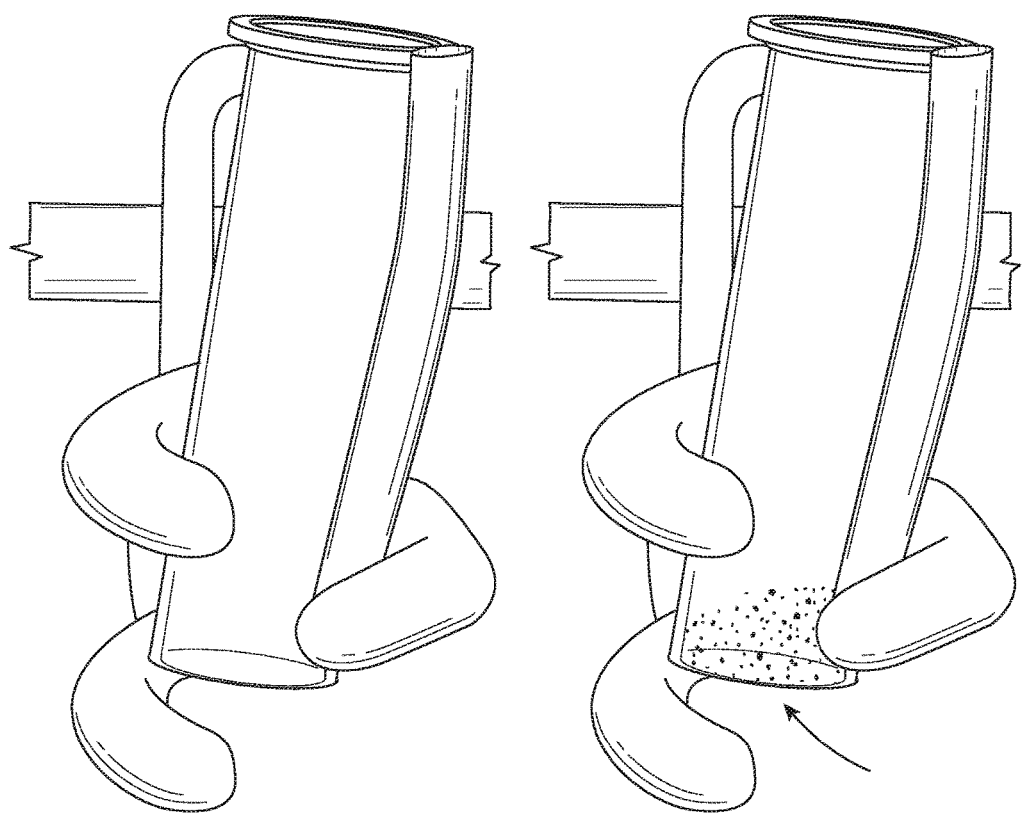

Preliminary data demonstrating this concept is shown in FIG. 4, in which a 5 ml syringe barrel 400 is used to simulate a fluid-filled space with a 3 mm dorsal vessel. A short length of tubing is connected to the syringe luer to keep the water in the syringe (4A). Prepolymer formulation is injected via the syringe into the open top of the syringe barrel. The prepolymer settles on the bottom of the syringe, and through reaction of water with the isocyanate, forms a foam (4B). The foam does not travel through the luer into the tubing at any point during the process (Arrow). The total expansion of this formulation is approximately 1.1–1.3×(final volume divided by initial volume) and the foam solidifies at approximately 120 seconds. This example demonstrates that prepolymer formulations can be deployed over lumbar arteries without embolizing, allowing bottom-up foaming.

In the simulation reflected in FIG. 4, the prepolymer formulation consisted of the following mixture, with actual mass amounts used for the aneurysm experiment in parentheses: 100 parts Nanopol® IP800 prepolymer (1.2 grams), 100 parts dimethylsulfoxide (1.2 g), 20 parts bis-(2-dimethylaminopropyl) ether catalyst (240 mg), 2 parts DABCO DC5098 surfactant (24 mg). In total, 0.5 ml of prepolymer formulation was injected.

Foam Delivery for Bottom-Up System

Because prepolymer formulation introduced into the lumen or cavity may collect at the bottom of the lumen or cavity, the tip of the delivery catheter must reside or be introduced at or near the top of the lumen or cavity so as not to become blocked with prepolymer formulation.

A number of mechanical methods for creating a bottom-up system may be employed, in addition to the chemical methods described above. For example, a balloon initially contained within the delivery catheter and released within the lumen or cavity can be inflated with a liquid, more dense than blood, and sink to the bottom of the lumen or cavity. The balloon is preferably sufficiently thin so as to obstruct only a very thin bottom layer of the lumen or cavity and the lumbar arteries. The balloon can be biodegradable, dissolvable, or permanent.

Similarly, a dense sheet, delivered through the delivery catheter can be deployed and will float or sink to the bottom of the lumen or cavity to provide a physical matrix onto which prepolymer cross-links or cures, preventing unacceptable migration of foam into the downstream vasculature. The sheet may be porous or non-porous (to water or blood, but not to the formulation), degradable or permanent.

Methods for Delivering a Bottom-Up Foaming System

Figure 5:
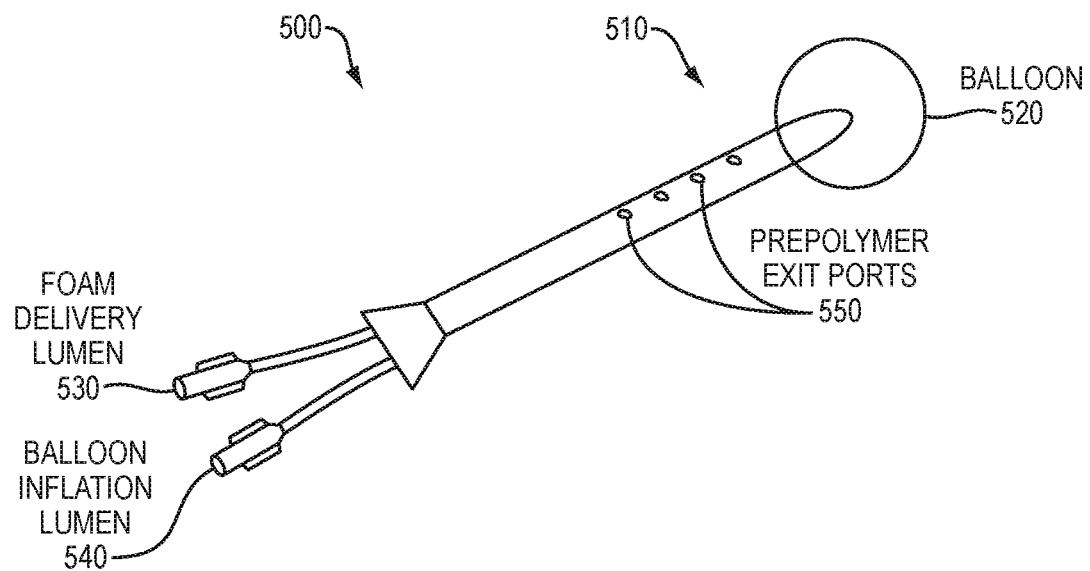
FIG. 5 depicts an example of a balloon-tipped catheter employed in a bottom-up foaming system.

A bottom-up foaming system can be delivered in any suitable way currently known in the art. For example, a bottom-up foaming system can be delivered utilizing a multi-lumen balloon catheter 500 as shown in FIG. 5. The catheter 500 includes separate lumens connected to separate foam delivery (530) and balloon inflation (540) inlets. The tip of the catheter includes at least one, and optionally more than one exit ports 550 fluidly connected to the foam delivery lumen 530 to permit in distribution of the in situ foaming formulation within the aneurysm sac, lumen or cavity.

In use, the tip 510 of the balloon catheter 500 is initially positioned within an aneurysm sac or other lumen or cavity and the balloon 520 is inflated with a biocompatible gas such as carbon dioxide, causing the tip 510 of the catheter 500 to migrate to the top of the lumen or cavity. An endoprosthesis (not shown) is then deployed while the balloon tip 510 remains at the top of the aneurysm sac, lumen or cavity. Following placement of the endoprosthesis, the in situ formulation is flowed through the foam delivery lumen and through the exit ports 550 into the aneurysm sac, lumen or cavity. The formulation sinks to the bottom of the fluid-filled aneurysm sac, lumen or cavity and generates a bottom-up forming foam, preferably sealing the bottom surface and filling some or all of the volume thereof. In some embodiments, the balloon 520 is deflated and the catheter removed. Alternatively, the balloon 520 is, in some cases, formed of a biodegradable material and is detached from the catheter 500 to degrade within the aneurysm sac, lumen or cavity. Alternatively, the balloon, made of a widely accepted biocompatible material, can detach and permanently reside in the lumen or cavity.

In some cases a bottom-up foaming formulation is delivered utilizing a catheter with a curved tip. Using this method, a delivery catheter with a curved tip is placed into the lumen or cavity such that the tip navigates around a vascular graft or other device to deliver prepolymer formulation ventral to the graft. The curvature of the catheter is, optionally, selectable by a user so that it can be straight when placed over a guidewire and becomes curved when the guidewire is released. The tip of the catheter optionally contains a radiopaque marker band or other feature that can be visualized using non-invasive means currently known in the art (e.g. fluoroscopy, ultrasound, magnetic resonance imaging, etc.) to facilitate visualization and placement of the catheter tip and/or the formulation and foam.

Venting Catheter

In other embodiments, a simple aspiration, or venting, catheter is positioned near or at the top of the lumen or cavity to provide an outlet for displaced blood and/or other materials displaced by the expansion of the foam. The tip of the catheter is generally positioned at the top of the lumen or cavity through the same mechanisms as the delivery catheter e.g., a balloon-tipped or curved catheter.

When utilizing a venting catheter, a low-expansion (preferably less than 1.3×, more preferably less than 1.1×) prepolymer formulation is injected in the presence of a venting catheter. Here, the venting catheter should be located at the top of the aneurysm, e.g. via a balloon as described above. As the formulation is injected, fluid is removed via the venting catheter. This is either out of necessity (if there is no other route of fluid removal), or periodically to assess the rate or volume of prepolymer formulation filling. The injection is stopped when prepolymer formulation is aspirated from the venting catheter, indicating that the formulation or foam has reached the top of the aneurysm. This is advantageous as it provides a simple means of determining the volume of injection without risking over-filling and foam embolization. This concept could also be applied to a top-down foam in which the venting catheter is placed at the bottom of the aneurysm.

There are numerous alternative embodiments of this invention, as described below.

Seal-and-Vent Foaming System

In one alternative embodiment, both the lumbar arteries and the IMA are occluded prior to the deployment of a prepolymer formulation that cross-links and cures to foam and which fills the aneurysm space and anchors the graft. In a preferred embodiment, this system makes use of a venting catheter that will evacuate the fluid from the lumen or cavity during foam deployment and expansion. This embodiment may consist of one or more prepolymer formulations as well as one or more additional devices. Any of the previously discussed strategies to transiently or permanently block the IMA could be employed to occlude the IMA. Any of the previously discussed strategies to transiently or permanently block the lumbar arteries could be employed to occlude the lumbar arteries. For example, a lumbar sealing prepolymer formulation used in the bottom-up system could be aerated, yielding a formulation that could both occlude the lumbars and the IMA. Such a prepolymer formulation would be advantageous as all major collateral arteries could be occluded with one formulation.

Co-Delivery of Endprostheses and Foams

In various embodiments of the present invention, both foams and endoprosthesis are delivered to sites of interest such as aneurysms. Endoprostheses are generally tubular bodies which may be compressible and/or self-expanding and which generally include a mesh or tubular framework. Exemplary endoprosthesis that are delivered and used with foams according to the present invention may include, without limitation, stent grafts and stents. These endoprosthesis are generally delivered using purpose-designed delivery catheters and, after their delivery, the foam is delivered to the space between the outer surface of the endoprosthesis and the inner surface of the lumen or cavity, as described above. However, in certain embodiments, the endoprosthesis and the foam are delivered simultaneously and/or using a single delivery device that includes a stent-delivery component (e.g. a balloon onto which the endoprosthesiss is carried in a crimped configuration) and a foam delivery component (e.g. a separate catheter or a branched catheter with a foam delivery lumen).

Pre-Formed Foam Plugs

In another embodiment, pre-formed foam plugs are delivered into the lumen or cavity via a catheter and are designed or intended to volumetrically expand upon contact with blood or other fluid. Depending on the cell and pore structure of the foam, the material properties may be tuned or adjusted to cause some or all of the plugs to float to the top of the sac to block the IMA. Alternatively, the material properties of the plugs may be tuned or adjusted to cause some or all of the plugs to sink to the bottom of the sac to block the lumbar arteries. Once the plugs are in place, in situ forming foam (ie., as a prepolymer formulation) is delivered into the lumen or cavity to the remaining voids.

Prepolymer Formulation Density Matched to Blood

In another embodiment, the density of the prepolymer formulation is precisely matched in advance of the procedure to that of the density of the patient's blood or fluid in the aneurysm sac, allowing for cross-linking, curing, or foaming to occur from the location of the delivery catheter tip outwards. In certain embodiments, the catheter is placed in the middle of the sac, resulting in the cross-linking, curing or foaming from approximately the middle of the sac outwards. Thus, fluid is pushed from approximately the center of the lumen or cavity outwards, allowing fluid within the lumen or cavity to escape via IMA and/or lumbar arteries. In addition, this approach results in the formulation having additional time to solidify prior to coming into close proximity to sac collateral vessels. The formulation could also be mixed with a diluent on-site based on the specific gravity of the patient's blood as measured by a medical professional prior to undertaking the procedure.

Dose Determination from Angiography

In another embodiment, radiopaque, low expansion prepolymer formulation is injected into the lumen or cavity via a delivery catheter until it reaches a particular fill level in the lumen or cavity as seen by angiography. A balloon or other marker could be placed indicating the top of the lumen or cavity. This is advantageous as it provides a simple means of determining the volume of prepolymer formulation injection without risking over-filling and foam embolization. This concept could also be applied to a top-down foam in which the marker is placed at the bottom of the lumen or cavity.

Foam with Chemical Carbon Dioxide Removal

For some formulations, particularly those with high expansions, a significant amount of carbon dioxide can be generated. Even with surfactants added to a formulation, there can be a high degree of off-gassing that occurs in which produced carbon dioxide is released from the rising foam/formulation. This off-gassing effect occurs because the surface and cellular structure are expanding/re-shaping during foam formation, and lack rigidity to retain the carbon dioxide.

The gas generated by the foam that is not captured within its structure may modulated by a variety of methods. For example, depending on the formulation 100% of the gas generated by the chemistry coalesce into bubbles/foam pores. Fluid is likely to eventually replace the gas, but this will occur over time. In another example, the formulation may only trap a portion of the gas generated by the chemistry therefore more off-gassing will occur and it will be more coincidental with the foam expansion process. In another embodiment, the amount of this free "off-gas" of carbon dioxide is reduced by inclusion of a buffering system, enzyme, or other means of consuming carbon dioxide gas at the point of generation. This will decrease the expansion and off-gassing of foams, obviating the need to specifically remove generated carbon dioxide. One example is the addition of calcium hydroxide to the formulation, which can react with carbon dioxide to form insoluble calcium carbonate.

Collateral Vessel Occlusion Fluid

In another embodiment, temporary or permanent occlusion of collateral vessels could be achieved with a fluid that is impermeable to forming foam due to phase separation from blood, high viscosity, or other means known to those skilled in the art. This layer could occlude either the lumbars or the IMA, depending on the density and other properties of the prepolymer formulation. Alternatively, the collateral vessels could be occluded with a commercially available embolic agent, such as Onyx® liquid embolic manufactured by Covidien.

Prepolymer Formulation Containing Particulates to Maintain Homogeneity

In another embodiment, the prepolymer formulation contains particulates, fibers, or other composite materials, inhibiting the ability of small bits of prepolymer formulation to separate from the bulk and embolize distal vessels.

Porous Membrane for Collateral Vessel Occlusion

In another embodiment, prepolymer formulation is delivered via delivery catheter and from within a porous balloon such that it reacts with water in the blood that has entered due to the porosity of the balloon. The pores of the balloon are sized such that the viscosity of the prepolymer formulation prevents it from escaping the balloon. When the balloon reaches its maximum fill, it will detach from the delivery catheter and either rise or fall (depending on the density of the enclosed foam), occluding either the IMA or lumbars.

Burstable Porous Membrane for Control of Embolization of Collateral Vessels

In another embodiment, prepolymer formulation is delivered into a perforated or porous balloon such that it reacts with water in the blood that has entered due to the porosity or perforated nature of the balloon. The perforations or pores are sized such that the viscosity of the prepolymer formulation prevents it from escaping the balloon. Preploymer formulation fills the inside of the balloon and begins to react. The foam is contained in the perforated or porous balloon until it reaches the capacity of the balloon, after which it will cause the balloon to burst or rupture at the perforations or pores and foam as a mass without pieces of foam embolizing off the main mass. The kinetics of the foam by the time it bursts out of the balloon is such that the foam is in a viscous cohesive state and has low risk of embolization.

Sheath-Core System

In another embodiment, a coaxial dual-lumen delivery catheter dispenses a first, outer formulation and a second inner formulation having a different composition and/or different foaming kinetics and mechanical properties. The kinetics and properties of these two prepolymers formulations are preferably tuned or adjusted in advance to generate materials that seal the collateral vessels while filling and displacing fluid within the aneurysm sac, lumen or cavity. For example, the sheath formulation can be a slow reacting, viscous material and the core material can be a buoyant, high-expansion formulation. When the material stream is dispensed at a sufficiently slow rate, a globular mass of material is formed at the delivery end of the catheter. The buoyancy of the core material causes the mass to rise to the top of the sac. The sheath material serves as a flexible skin to contain the inner material. The mass grows as the inner material begins expanding. The layer thickness of the outer material decreases as the mass grows. Finally, the mass reaches the top of the sac and seals off or occludes the IMA. Alternatively, these two prepolymers are mixed together and form a coaxial structure by phase separation (e.g., water-miscible and oil-miscible phases).

Thrombin

In certain embodiments of the present invention, after placement of a vascular graft, thrombin is injected into the lumen or cavity to cause thrombi to form in the collateral vessels. Excess thrombus can be aspirated out of the lumen or cavity through an aspiration catheter. A prepolymer formulation can then be delivered into the lumen or cavity via a delivery catheter.

Acid-Based Reactions

In an alternative embodiment of this invention, acetic acid and sodium bicarbonate are mixed and caused to react together in situ to produce carbon dioxide as a blowing agent. An additional by-product of the reaction is water, which can accelerate an independent isocyanate gelling reaction.

In some cases, the foams of the present invention may be described as "lava like" in that they are viscous, yet flowable, and harden from the exterior surface towards the interior. The external skin of the foam forms as a fast-forming, robust, balloon-like outer layer that encases the inner polymer formulation This promotes material cohesion and resists deformation and movement outside the targeted are, including, for example, migration into collateral vessels. The external skin of the foam may deform during expansion to expose at least a portion of the inner polymer formulation, which may then react upon contact with the external environment to reform the external skin. As used herein, the outer layer of the foam may be referred to as a "skin" that consists of a thin exterior layer that is harder (e.g., more solid, less flowable) than the material contained within that outer layer Additionally, the skin may be characterized as "robust" due to mechanical properties (e.g., strength, toughness, etc.) that are different, at least for some period of time, than the material contained by the skin The formulation within the interior tends to harden via the same process as the skin, albeit more slowly.

The skin may form rapidly to produce a material that is not cohesive in-situ, resulting in a continuous, packable polymer, which may tend to form coils Continued extrusion of the formulation out of a delivery device such as a catheter or micro-catheter may allow a user to create long/sustained/continuous coils to partially or completely fill an aneurysm or other bodily cavity.

In a preferred embodiment, the foam is formed by a fast cross-linking reaction that can be surface triggered by in situ water For example a liquid silicone rubber prepolymer formulation that cures and foams at room temperature is formulated for filling of aneurysmal space Such formulations produce foam by liberation of hydrogen gas from a reaction of silicone hydrides in the presence of tin or platinum catalysts Silicone hydride reaction can be coupled with hydrosililation reaction to generate two-part systems that produce elastic silicone foams upon mixing Multifunctional moisture sensitive silanes are one example of materials susceptible to such reactions especially when formulated with tin, titans or other metal-organic catalysts One-part cross-linking systems can be created by a two-step process In the first step, hydroxyl containing siloxanes (either silanols or carbinols) are reacted with an excess of multifunctional silane containing acetoxy, oxime, alkoxy (e.g., methoxy, ethoxy), isopropenoxy, amide, amine, aminoxy, or other functional groups containing silane with the hydrolytically susceptible Si—O—C bond. The resulting prepolymers have multiple groups that are susceptible to hydrolysis In the second step, such prepolymers are exposed to in situ water to result in a rapidly cross-linking elastic solid The reaction proceeds from the outside-in, resulting in a quickly formed outer skin and, in some cases, the formation of the foam into a coil-like configuration The slower permeation of water or alternative reaction trigger can be used to slowly cure the material inside of the skin The proteins and pH of the blood can be used to support coil formation by modifying the rate of the skin-forming reaction as well as in coating the formed coil and preventing coil sticking and agglomeration upon self-contact.

Additionally, hydride functional (Si—H) siloxanes or isocyanate functionalized carbinols can be introduced into silanol elastomer formulations to generate gas and produce expanding foamed structures Expansion of the material can be used to increase the size of the formed coil effectively decreasing coil embolization potential Expansion of the material can also be critical to increase material size without delivery of more material, in adding porosity and in generating sealing or pressure Additional formulation ingredients such as surfactants can be used to the impact of generated gas on porosity and expansion.

Alternatively, isocyanate-containing prepolymers are a second example of materials that may be used to generate in situ forming coils or lava-like foams Isocyanate groups are relatively unstable when exposed to water and moisture One-part isocyanate based cross-linking systems can be created by a two-step process In the first step, polyols, dials, diamines, polyamines, diepoxides, silanols, carbinols or polyepoxides are capped with aliphatic or aromatic diisocyanates such as isophorone diisocyanate (IPDI), hexamethylene diisocyanate (HDI) and methylene diphenyl diisocyanate (MDI) Additionally, multifunctional isocyanates such as HDI biuret, HDI trimer, and polymeric MDI can be combined with dials or diamines The resulting prepolymers have multiple distant isocyanate groups that are able to react with water and amines found in blood In the second step, such prepolymers are exposed to in situ blood resulting in rapid cross-linking and foam formation The reaction is water-triggered and proceeds from the outside-in, forming a porous outer skin, lava-like shell core structure that assists in coil formation The expansion of such materials can be important in generating coils of a large diameter while maintaining a small cross-sectional area of the delivery device Such materials can be used to form stand-alone foaming or gelling coils or combined with each other such that one material is coaxially formed on top the other. For example, a coaxial delivery device can deploy a coil forming formation surrounded by a highly expandable coating formulation The two formulations may be from different chemistry classes Alternatively, the two formulations may be selected to be immiscible such that upon delivery the formulations phase separate (eg., oil miscible and water miscible formulations) to naturally form a coaxial structure. Additionally, the interaction with the catheter wall and/or the density differential of the two fluids can be used to further drive the phase separation. Additionally, two part formulations may be designed such that the two parts are not fully miscible. A surfactant system may be used to formulate the two part formulation into a single stable emulsion. Such an emulsion could be delivered via single chamber delivery device and does not require mixing. The emulsion can be destabilized by shear during delivery or in situ factors (pH, temperature, ionic strength). Upon such destabilization, the internal phase of the emulsion would spill out and trigger the reaction with the external phase resulting in in situ foam formation.

The solidification of interior portions of foams that form with an exterior skin can be controlled, for example, by altering the permeability of the material to solidification trigger. In the case that the trigger is water, permeability can be controlled by adjusting material hydrophobicity. Additional ingredients can be added to adjust material radiopacity, density, and/or contact angle with blood, tissue, or other biological matrices.

Figure 6:
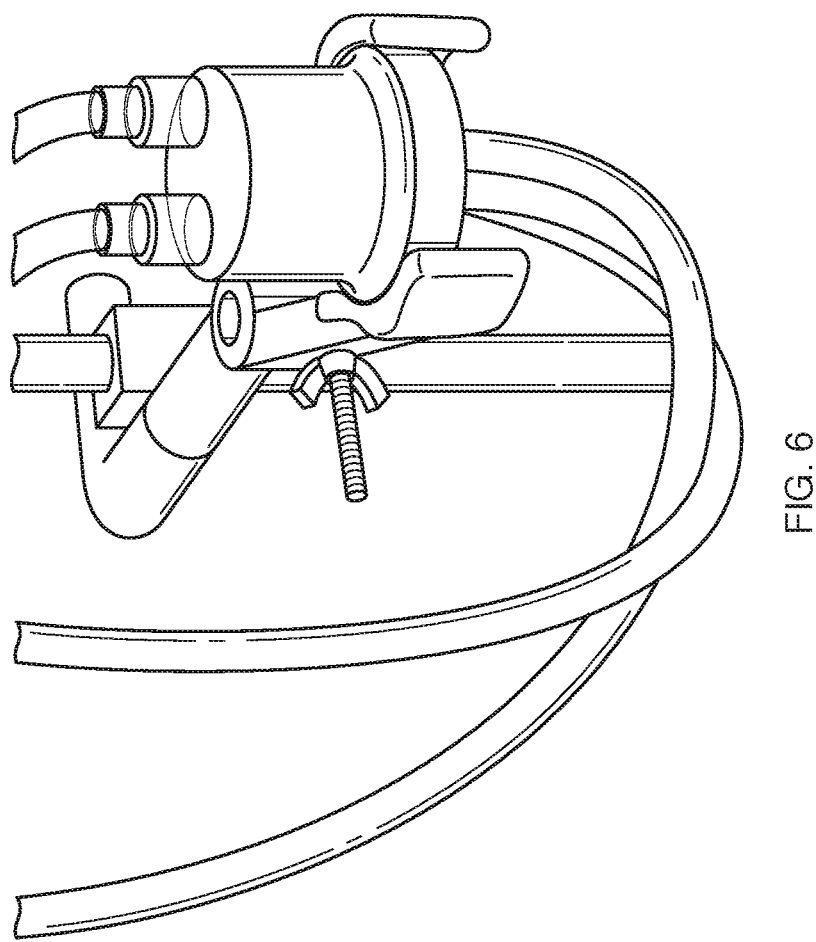
FIG. 6 shows an example of deployment of the siloxane formulation demonstrating good fill and low embolization. The injected reaction mixture does not travel down the 4 mm lumbar arteries, or up the 5 mm port simulating the IMA.

This embodiment is demonstrated in the model photographed in FIG. 6. In this figure, a 40 ml container is used to simulate a fluid-filled aneurysm space. Tubing connected to the top and bottom is used simulate collateral vasculature. Two 4 mm ID tubes attached at the bottom of the container are used to simulate lumbar vessels and an 8 mm tube attached to the top of the jar simulates the IMA. A siloxane formulation is injected via an injection port at the top of the vessel. The formulation fills the chamber from the bottom up and reacts to form an elastic and solid foam. The foam forms through the reaction mechanism.

The foam does not travel through the collateral tubing attached to the bottom of the reaction chamber. Fill is stopped prior to material traveling up the superior tubing simulation of the IMA. The total expansion of this formulation is less than 50% and the foam solidifies in under 5 minutes. This example demonstrates that siloxane formulations can be deployed over lumbar arteries without embolizing them, allowing bottom-up foaming. In this example, the prepolymer formulation consisted of the following mixture: 80 parts vinyl terminated polydimethylsiloxane, 20 parts methylhydrosiloxane dimethylsiloxane copolymers and 0.5 parts platinum Karstedt catalyst.

The present invention offers advantages not previously known in the art. For example, use of the invention will allow for: i) the ability for delivery into a closed, fluid-filled lumen or cavity (intravascularly); ii) the ability to seal collateral vessels and aneurysm sites from retrograde flow and defects, malposition or damage allow flow through endovascular graft(s); and iii) the ability to displace blood or other fluids from a space in a safe, highly-controlled, and repeatable fashion. Moreover, the present invention provides the ability to anchor an endovascular graft in place in that i) the prepolymer fills available space while conforming to the stent graft; ii) by preventing leaks, the foam stabilizes the graft at its proximal and distal ends; and iii) it is applicable to complex geometries. Among the commercial applications of the inventions are: prophylactic treatment of Type II endoleaks; treatment of type I, II, or IV endoleaks instead of an open surgical procedure; and stabilization of stent grafts following intravascular aneurysm repair.

Delivery Systems for In Situ Forming Foams Generally

Delivery systems of the invention also include modifications to the delivery catheter to more effectively deliver foam. For example, in some embodiments the delivery catheter includes tips adapted to deliver foams having specific shapes or dimensions.

As used herein, "outer catheter" refers to the catheter defined by the outer most walls of the delivery catheter. As used herein, the term "inner catheter" refers to a lumen of any size or shape that is contained within the wall of the outer catheter. An inner catheter may be detached from and contained within the wall of the outer catheter, or it may be attached to the wall of and/or share a wall with the outer catheter. In some embodiments, the delivery system comprises an outer catheter with one or more inner catheters contained within. In some embodiments, the two or more inner catheters may be separate from each other, while in other embodiments one inner catheter may be contained concentrically contained within another inner catheter. In other embodiments, the inner catheters themselves contain multiple lumens. The inner catheters are preferably 3 to 10 Fr, more preferably 3 to 5 Fr. In yet more embodiments, the inner catheters may share a wall with each other and/or with the outer delivery catheter. The inner catheters may be moved independently of each other and of the outer catheter in a rotational or longitudinal fashion. The inner catheters may be the same shape as each other or the outer catheter (i.e. concentric circles), or may be different shapes. For example, as shown in FIG. 8, an exemplary delivery catheter 800 includes an inner catheter 810 with an oblong shape that is able to rotate within a substantially round outer catheter 820, thereby mixing the contents of the outer catheter 820. The wall of the inner catheter 810 may be comprised of the same or different material as that of the wall of the outer catheter. The inner catheter 810 may deliver any fluid including the one or more components of an in situ foaming formulation and/or a gas for entrainment into the formulation or incorporation into the foam. In some embodiments an inner catheter delivers contrast agent. In another embodiment, the inner catheter delivers the prepolymer fluid while the outer catheter delivers contrast agent. In some embodiments, the inner and outer catheters deliver two or more different types of pre-polymer, which can either mix or output a stream of material that is comprised of an outer layer of pre-polymer and an inner layer of a different pre-polymer. The kinetics and properties of these two or more pre-polymers can be tuned to generate materials that seal the collateral vessels of an abdominal aortic aneurysm, as a non-limiting example. For example, the outer catheter material can be a slow reacting, viscous pre-polymer and the inner catheter material can be a buoyant, high-expanding pre-polymer. When the catheter delivers the pre-polymers at a slow rate, a globular mass of material is formed at the end of the catheter. The buoyancy of the core material causes the mass to float to the top, with the outer catheter material serving as a flexible skin to contain the inner catheter material. The mass grows as the inner catheter pre-polymer starts expanding, and finally, the mass reaches the top of the aneurysm sac and seals off the IMA. In other embodiments, one or more lumens may run for only a portion of the length of the catheter to facilitate rapid exchange on guide wires, for example.

In certain embodiments of the invention, the pre-polymer delivery system includes a pressure sensor on the proximal or distal end or both of the delivery catheter to enable determination of successful treatment. In some embodiments the pressure sensor is incorporated into the needle or catheter, while in other embodiments the pressure sensor is separate and is used in conjunction with the needle or catheter. In certain embodiments, the user of the delivery system sets a pre-determined pressure level for the space or body cavity where the pre-polymer fluid is to be delivered. It is preferable to use a pre-polymer fluid with foaming characteristics such as short rise time or low expansion ratio, so that pressure feedback is rapid and delivery controllable.

In other embodiments of the invention, successful application of the pre-polymer fluid is determined by filling the space with a contrast material prior to delivery of the pre-polymer fluid to estimate the space available. Then, the appropriate amount of pre-polymer fluid is loaded into the syringe or catheter based on its expansion characteristics.

Delivery systems of the invention may also be designed so that a venting lumen or venting catheter is included to aspirate gas or fluid generated from the foaming reaction and/or blood from the target space. The tip of the venting catheter or lumen is specially designed to prevent clogging by foam components, clots or other material within the target space. In some embodiments the distal end of the catheter has at least one fenestration in the wall of the catheter to enable entry of gas or fluid. In some embodiments such as those shown in FIG. 9, the inner catheter 910 includes a plurality of fenestrations 915, and in still other embodiments, the distal end of the inner catheter 910 has includes a distal mesh section 916 that is optionally articulating. The plurality of fenestrations or mesh construction are preferably confined to the distal 10 cm of the inner catheter 910, and more preferably the distal 5 cm thereof. An outer, coaxial catheter 920 covers this distal end of the catheter which can be advanced and retracted along the length of the distal end of the catheter to remove foam material which may clog openings into the delivery space. In use, if the fenestrations 915 or mesh 916 clogs during the delivery of a formulation, the inner catheter 910 is simply advanced relative to the outer catheter 920 to expose additional, unclogged portions of the inner catheter 910. Alternatively or additionally, the inner catheter 910 is retracted and advanced repeatedly relative to the outer catheter 920 to dislodge any material clogging the fenestrations 915 or mesh 916.

In some embodiments, where the distal end of the catheter has one or more fenestration or is composed of mesh, one or more catheter steering wires (not shown) can be incorporated to deflect the distal tip of the catheter. By alternately flexing the distal portion of the catheter with the steering wire or wires, any foam, polymer, clot, pre-polymer, or any other obstruction which is covering the mesh or fenestration may be dislodged so the holes allow passage of gas or fluid from the delivery space into the catheter lumen. Gas or fluid may passively move out of the space by a pressure gradient between the delivery space and ambient atmosphere or below atmospheric pressure can be applied to the proximal end of the catheter lumen to facilitate removal of excess gas or fluid from the delivery site. Negative pressure or a pressure drop may be created by pumps known to those skilled in the art, for example, bellows, rotary pump, syringe, diaphragm pump, etc. The catheter walls may be reinforced to prevent lumen collapse or the pressure drop would be limited not to exceed that which will collapse the lumen. The distal end of the catheter may be tapered or have reduced or gradually reducing diameter to reduce the resistance to gas or fluid flow out of the delivery space.

In some embodiments of the foam delivery system, the catheter has a one-way passive valve which prevents blood, water, or saline from wicking or otherwise entering the distal end of the catheter and reacting with the pre-polymer liquid prior to its delivery. Alternatively, a user-activated distal valve may be included, using a balloon disposed at least partially within the distal tip to occlude the catheter. FIG. 10 illustrates such a balloon valve catheter 1000 which includes a delivery lumen 1010, an inflatable balloon valve 1020 fed by a balloon lumen 1030, and an optional guidewire lumen 1040. The balloon valve 1020 may include any material, compliant or non-compliant, and is generally sized to achieve a good conformal fit with the delivery lumen 1010 of the catheter 1000.

In some embodiments, an inner catheter can move independently of the wall of the outer delivery catheter and the end of the inner catheter may extend past the end of the outer delivery catheter or may retract back into the delivery catheter. A flexible, collapsible hood 1110, as shown in FIG. 11, below, can be used to connect the outer catheter 1120 of the delivery catheter 1100 to the outer wall of the inner catheter 1130. To apply the foam, the inner catheter 1130 is extended past the edge of the delivery catheter wall to unfurl the flexible hood 1110. The in situ foaming formulation is then dispensed through the inner catheter. After, the inner catheter is retracted into the delivery catheter, and the flexible hood collapses to occlude the outer delivery catheter. This flexible hood system is used to prevent drips and to ensure that no foam remnants remain on the outside of the delivery system.

In another embodiment, an inner catheter is rotatably disposed within the outer catheter and, along at least a portion of the length of the catheter, the outer wall of the inner catheter is closely apposed with the inner the wall of the outer catheter. In this arrangement, substantially no space exists between the walls of the inner and outer catheter. The distal ends of both inner and outer catheters are preferably sealed, and each of the inner and outer catheters preferably include at least one opening (e.g. a slit or fenestration) at or near the same position along the proximal-axis of the catheter. In this arrangement, the inner catheter is rotably or longitudinally moved within the outer catheter, the fenestrations align to permit an in situ foaming formulation to be discharged from the inner catheter into the body; the discharge is then stopped by moving the inner catheter so that the at least one opening of the inner catheter is no longer aligned with the at least one opening of the outer catheter. An endoflater or medrad is optionally used to provide additional pressure for delivery, if desired or necessary in this or any other embodiment of the present invention. In other embodiments, the number and shape of openings, on the inner and outer catheters is selected so that changing the position of or rotating the inner catheter in relation to the outer catheter can direct the flow rate, direction, and shape of pre-polymer fluid. For example, if the inner and outer catheters both have a slit 5 mm×1 mm, moving the inner catheter longitudinally in relation to the outer catheter would make the opening smaller or larger lengthwise, and moving the inner catheter rotationally in relation to the outer catheter would make the opening smaller or larger widthwise.

In other embodiments, the outer surface of the outer catheter has a coating which prevents or minimizes adhesion to unreacted, partially-reacted, or fully-reacted foam. This coating can be on the entire catheter length or just the distal portion expected to come in contact with the foam. Where the coating is just on the distal portion of the catheter, it is applied preferably along the distal most 10 cm of the delivery catheter, and more preferably along the distal most 5 cm of the delivery catheter.

In other embodiments, the inner or outer catheter is designed to deliver energy to the solution in the other catheter, such as heat or light. For example, in FIG. 12, the formulation in the inner catheter 1210 reacts to heat, and thus the outer catheter 1220 carries warm fluid of a certain temperature. In FIG. 13, the formulation in at least one of the inner and outer catheters 1310, 1320 reacts to ultraviolet light, and the walls of the inner catheter 1310 are light-permeable. Once UV light is carried into either the inner catheter 1310 or the outer catheter 1320, for instance via a fiber-optic element, the formulation or formulations react, for example to initiate the formation of the foam.

Outer catheters according to various embodiments of the invention are used as guide catheters to facilitate the placement of the inner catheter within a delivery site. An example of this is seen in FIG. 14, where outer catheter 1410 is threaded through the vasculature to a position proximate to a stent graft 1420; once positioned, the inner catheter 1430 is threaded by the stent graft 1420 into an aneurysm to be filled with foam. The outer catheter 1410 according to this example is characterized by, among other things, sufficient steerability and column strength to be threaded through the vasculature; it is optionally configured to travel over a guidewire, further facilitating accurate placement of the inner catheter 1430.

In other embodiments, such as the one illustrated in FIG. 15, a delivery catheter 1500 includes an outer catheter 1510 which is retractable relative to two or more separate, flexible inner catheters 1520. The inner catheters 1520 are, preferably, smaller than 5 Fr, and more preferably 3 Fr or smaller, and are preferably less than 10 cm long, more preferably less than 5 cm long. In some embodiments, the inner catheters 1520 are curved such that when placed into the aneurysm sac, the sub-catheters each laterally circumvent a pre-placed endoprosthesis 1530 such as a stent graft. The curvature of the inner catheters 1520 is generally selected to permit their respective distal tips to be positioned to one side of the endoprosthesis (e.g. the ventral side), where two or more streams of an in situ foaming formulation are then delivered within a relatively contained volume. In other embodiments, the curvature of the inner catheters 1520 are selected so that, when deployed, the inner catheters 1520 are oriented in different directions to distribute the formulation throughout a larger space.

The outer catheter 1510 optionally includes a retractable sheath 1515 slidably disposed over at least a portion of the length of the inner catheters 1520 to provide mechanical support to the inner catheters 1520 during navigation to a site where the deposition of foam is desired. After the tip of the delivery catheter 1500 is in the desired location, the sheath 1515 is retracted to expose the two or more inner catheters 1520. Multiple inner catheters 1520 according to this embodiment may have advantages relative to arrangements in which a single, relatively larger catheter is used: for instance, multiple smaller-gauge inner catheters 1520 would cause less distortion of the seal between an endoprosthesis and the surrounding tissue than would be experienced with a larger catheter, while providing substantially the same cross sectional area for delivery of the formulation.

The invention disclosed herein is further particularly suited to deliver foams not only into empty spaces, but into fluid-filled spaces as well. As used herein, the terms "top" and "bottom" refer to the gravitational top and bottom of the cavity being filled with foam. For example, the top refers to the point at which air would collect in a fluid-filled cavity. As prepolymer foam is introduced into a fluid-filled aneurysm sac, the foam may either expand from the top downward, or from the bottom upward.

In the case of EVAR, the objective is to fill the aneurysm space surrounding a stent graft as completely as possible, including occluding possible routes of fluid entry via collateral vessels, the dorsally-located lumbar arteries, and the ventrally-located inferior mesenteric artery (IMA). Occlusion of the lumbar arteries and IMA prevents unwanted endoleak, which can result in morbidity, mortality, and/or additional medical care and expenses. A challenging aspect of this problem is the need to occlude the collateral vessels but also evacuate the fluid contained initially within the aneurysm. Failure to occlude a vessel could reduce efficacy, while occlusion prior to fluid evacuation could result in an unacceptable pressure increase and possible acute endoleak and/or aneurysm rupture. The invention described herein is particularly suitable for occlusion of the IMA and lumbar arteries without unacceptable migration of the foam into downstream vasculature.

In one embodiment of the invention, the delivery catheter has a slit running parallel to the direction of the long axis of the delivery catheter, which delivers pre-polymer in a stream wide enough to prevent pre-polymer from migrating into the downstream vasculature by forming foam in pieces too large to embolize in the IMA or lumbar arteries.

In another embodiment, a balloon or bag is contained within the catheter and is delivered to the aneurysm sac, and then is subsequently released within the aneurysm sac. The balloon may be installed in the catheter lumen prior to insertion of the catheter inside the body, or the balloon may be pushed through the catheter lumen after the catheter is inserted inside the body. It can be inflated with gas or a low density liquid (<1.05 g/ml) which is provided through the delivery catheter. Once inflated, the balloon floats to the top of the aneurysm sac and is sufficiently thin so as to obstruct only a very thin top layer of the sac and the IMA. In another embodiment the balloon is filled with a fluid more dense than blood, and sinks to the bottom of the aneurysm sac upon inflation. The balloon should be sufficiently thin so as to obstruct only a very thin bottom layer of the aneurysm sac and the lumbar arteries. As such, the balloon, which is preferably detachable from the catheter, interferes only minimally with the geometry of the normal aneurysm. The balloon can be biodegradable, dissolvable, or may not be biodegradable or dissolvable. In another embodiment, the balloon is small enough to be placed inside the IMA or lumbar arteries.

In another embodiment, illustrated in FIG. 16 the balloon 1610 is perforated and is positioned over the lumbar arteries 1620 before being filled with saline. Due to the perforations, water is allowed to exit the balloon, but the balloon 1610 maintains an unfurled and semi-inflated state. The saline initially injected into the balloon 1610 may contain slightly higher salt concentrations than blood so that by way of osmosis, water tends to travel into the balloon 1610, keeping it in a relatively inflated state. Pre-polymer is then injected into the balloon 1610, reacts with water and foams, providing a blockade over the lumbar arteries. The balloon 1610 may dissolve, may be resorbable, or may be permanent.

Similarly in another embodiment, a buoyant sheet, delivered through the catheter, can be deployed and float to the top of the aneurysm sac (blocking the IMA opening) to provide a physical matrix onto which pre-polymer attaches, preventing unacceptable migration of foam into the IMA and downstream vasculature. The sheet may be made from the same polymeric material as the foam, or of a different suitable polymeric or non-polymeric biocompatible material. In another embodiment, a dense sheet is delivered through the catheter, which after deployment via unfurling, opening or other suitable deployment mechanism, floats to the bottom of the aneurysm sac (blocking the lumbar arteries) to provide a physical matrix onto which prepolymer gets attached, preventing unacceptable migration of foam into the downstream vasculature. The buoyant sheet can be porous or non-porous, and can be biodegradable, dissolvable, or may not be biodegradable of dissolvable. In other embodiments, the sheet is semi-permeable, and allows gas, and potentially blood to pass through, but not the pre-polymer fluid or foam.

In some embodiments, the delivery catheter further comprises a balloon located at the distal end. The balloon is initially delivered to the aneurysm sac and the balloon is inflated with any biocompatible gas, such as carbon dioxide, which carries the tip of the delivery catheter to the top of the aneurysm sac. The vascular graft is then deployed and the balloon catheter tip remains at the top of the sac. The distal end of the catheter may contain one or more fenestrations along the length of the catheter to deliver the pre-polymer within the sac from the bottom up. The one or more fenestrations are preferably located within the most distal 10 cm of the delivery catheter, and more preferably between the most distal 10 cm and the most distal 5 cm. Then, the balloon is deflated and the catheter is removed. In another embodiment, the balloon can detach and is left behind to be resorbed by the body. In other embodiments, the balloon is made of a biocompatible material and therefore can detach and permanently reside in the sac.

In some embodiments, the balloon is porous and filled with pre-polymer fluid after the delivery catheter reaches the delivery destination. The pores are sized such that the viscosity of the pre-polymer prevents it from leaving the balloon, but water, saline, or blood may enter the balloon to react with the pre-polymer fluid to produce foam. Once the foaming is complete, the balloon can be detached from the catheter and will rise or fall, depending on the density of the enclosed foam, and will occlude either the IMA or the lumbar arteries. The pores of the balloon are preferably larger than a water molecule and smaller than the size of the prepolymer molecule. In other embodiments, the balloon is designed to contain the expanding foam and burst once the foam reaches a certain volume, to help the foam stay in a cohesive state, thus lowering the risks of loose foam particulates within the vasculature.

Sometimes, a narrow catheter tip is necessary to reach small spaces, but once there, a larger gauge aperture is necessary for dispensing foam. Thus, in some embodiments such as the one illustrated in FIG. 17, the distal tip of the delivery catheter 1700 is a relatively narrow gauge (for example 5 Fr), and includes a design feature such as an inflatable balloon 1710 or a shape-memory structure which expands to define a substantially larger space and/or a larger gauge aperture (for example 28 Fr) for dispensing foam.

It may be desirable, in some cases, to encase at least a portion of the foam in a membrane or other structure, for instance to ensure the delivery of a precise volume of foam or to conform the foam to a specific shape. This is achieved in some cases, by flowing an in situ foaming formulation into a membranous bag or pouch, which is optionally connected to the distal tip of the delivery catheter. For instance, as shown in FIG. 18, the distal tip of the delivery catheter 1810 includes a detachable membrane 1820 defining a pouch for containing the formulation and the foam. After the distal portion of the delivery catheter reaches the space where foam is to be applied, the in situ foaming formulation is flowed into the membrane 1820, where it then reacts to form the foam, which may either partially or completely occupy the volume defined by the membrane 1820. In some embodiments the membrane is packed into the distal tip of the delivery catheter in a space saving shape, such as rolled, stellate, folded, etc., which then expands into a larger final shape or orientation when filled with foam. Exemplary space saving shapes are illustrated in FIG. 18. In certain cases, as the membrane 1820 is filled, back-pressure caused by the expansion of the foam within the membrane may cause form to recirculate into the catheter; this is prevented, in some cases, by the inclusion of a check valve 1830 within the distal portion of the delivery catheter 1810.

In one example, the device is an ePTFE tube that is crimped, so that it possesses sufficient stiffness to withstand delivery forces, as shown in FIG. 19.

In some embodiments of the invention, one or more inner catheters are used to remove gas or fluid from inside the body, for example to provide an outlet for blood displaced by the foam, or to provide an outlet for gas released by the foaming action. The venting rate should be approximately equal to the delivery rate of the pre-polymer fluid, so that the volume within the aneurysm sac remains constant. As used herein, a venting catheter is one which is used to remove gas, fluid, or other materials from within the body. In other embodiments, the venting catheter is introduced separately from the pre-polymer foam delivery catheter, for the purpose of removing gas or fluid. For example, in one embodiment a catheter, preferably less than 5 Fr, is introduced contralateral to the delivery catheter. In other embodiments where the foam is a low expansion foam (preferably less than 1.3 more preferably less than 1.1) which is to expand in a bottom-up fashion, the venting catheter is introduced to the top of the sac using a balloon as described herein and is used to monitor the rate of pre-polymer filling. As the pre-polymer fills the aneurysm sac, the user of the delivery system ceases delivery of the pre-polymer fluid once pre-polymer begins to be aspirated from the venting catheter. This is advantageous as it provides a simple means of determining the volume of pre-polymer fluid to be deposited without risking over-filling and foam embolization. This embodiment can be applied inversely to a top-down foam in which the venting catheter is placed at the bottom of the aneurysm sac.

In other embodiments, the gas removal is achieved by the inclusion of a buffering system, enzyme, or other means of consuming carbon dioxide gas at the point of generation. This decreases the expansion and off-gassing of foams, which obviates the need to specifically remove carbon dioxide that is generated by the foam. One example is the addition of calcium hydroxide to the formulation, which can react with carbon dioxide to form insoluble calcium carbonate. In some embodiments, after placement of the vascular graft, thrombin can be injected into the aneurysm sac to cause thrombi to form in the collateral vessels. Excess thrombus can be aspirated out of the sac through the venting catheter. Pre-polymer can then be delivered into the sac. A portion of the catheter, steering wire, coaxial sheath, or other attachment to the distal end of the catheter can be advanced into the foam near the gas relief catheter to burst cells in the foam to release additional gas. This can allow pressure building up in the foam cells to be released and evacuated through the venting catheter.

In some embodiments of the invention, the distal end of the delivery catheter contains a self-expanding mesh cylinder which is initially compressed, and expands once it is deployed. The mesh cylinder may be comprised of a braided material, such as nitinol, that selfexpands. The mesh cylinder could have a ring on one or more rings on the end or throughout the cylinder to allow it to self-expand. The cylinder may also have a spiral running along its length to allow it to self-expand both radially and longitudinally. In certain embodiments, the rings and spiral can be made of nitinol, or another material known in the art which has similar shape memory. In some embodiments, the mesh cylinder has a pore size such that pre-polymer fluid and foam will not pass through, but blood and other fluids are able to pass through. For example, the pores may range in size from 50 to 100 microns. A venting catheter may also be used in certain embodiments to evacuate blood or other fluid in the event that the mesh clots over and prevents fluid escape. The mesh ring is sized such that it will block all collateral vessels and not interfere with the landing zone of the stent graft. For example, the length of the ring may be shorter than the aneurysm length such that it does not extend into the healthy portion of the vessel where the distal and proximal ends of a stent graft would be positioned. In other embodiments, a long foam filament is used instead of a mesh cylinder and is delivered in a highly compressed form and encased in a dissolvable membrane. After the filament is deployed by the user, it coils around the space and expands to fill the space. The foam may or may not have a core of a different material to help give it mechanical strength. The filament may also have a coating such as a hydrogel which swells upon contact with water.

In some embodiments of the invention, the delivery catheter may be loaded with collateral blocking pre-formed foam plugs which can expand volumetrically upon contact with blood. Depending on the composition of the foam or its cell and pore structure, the material properties may be tuned to cause the plugs to float to the top of the sac to block the IMA. Alternatively, the material properties of the plugs may be tuned to sink to the bottom of the aneurysm sac to block the lumbar arteries. This is depicted in FIG. 20. Once the foam plugs are in place, in situ forming foam is delivered into the aneurysm sac to fill the remaining voids. In an alternate embodiment, the collateral blocking plugs can be formed in situ.

Free Release Catheters for Delivery of Embolizing Foams

According to certain embodiments of the invention include features that facilitate the precise delivery of embolizing in situ forming foams, for example by preventing catheter clogging during or leakage during the delivery of in situ foaming formulations. Referring to FIG. 21, an exemplary delivery catheter 2100 according to certain embodiments of the invention includes concentric inner and outer catheters 2110, 2120. The outer catheter 2120 includes a conventional distal aperture 2121, while the inner catheter 2110 has a sealed distal end and instead includes at least one side aperture 2111 through which a formulation may be dispensed. Delivering in situ foaming formulations through side aperture 2111 may have several advantages, including the ability to deploy the formulations in close apposition to the walls of a lumen or cavity, and the ability to deliver the foam in a direction that is perpendicular to the flow of fluid within a lumen, thereby reducing the migration of the resulting foam in the direction of flow within the lumen.

In use, the formulation is dispensed slowly, to permit foam forming reactions (e.g. blowing and/or gelling reactions) to take place. In some cases, such as the "lava-like" foams described above, the foam is characterized by a skin or shell that impart rigidity to the foam, and the slow delivery of the in situ foaming formulation permits the gelling and/or blowing reactions necessary to form the foam skin to take place. In these cases, the foam may remain attached to the delivery catheter 2100 after it is dispensed, in a manner similar to an extrusion process. To remove the foam, the inner catheter 2110 is simply retracted into the outer catheter 2120. Removal is optionally facilitated by the use of a hydrophobic coating on the distal portions of the inner and outer catheters 2110, 2120.

In certain cases, it may be desirable to deliver a delivery catheter according to the present invention over a guidewire and to dispense the formulation through a side aperture. Referring to FIG. 22, an exemplary delivery catheter 2200 adapted for over-the-wire delivery includes a one-way valve 2210 disposed at the distal tip of the delivery catheter 2200, as well as at least one side aperture 2220 for discharging an in situ foaming formulation. The one way valve 2210 is configured to permit material to pass through and into the distal tip of the delivery catheter 2200, but to resist the movement of material through and out of the distal tip. The one way valve 2210 can have any form currently used in the art, including a duckbill valve (FIG. 22A), a reed valve (FIG. 22B), or a slit (FIG. 22C) formed within an elastomeric material.

In use, a provider threads a guidewire through a body lumen to a place where deposition of foam is desired, then threads the distal end of the delivery catheter 2200 over the guidewire and advances the delivery catheter through the vasculature to the delivery site. The guidewire is then retracted through the delivery catheter 2200, and the one way valve 2210 seals after it is withdrawn. The in situ foaming formulation is then flowed through the catheter and out the at least one side aperture 2220 into the body lumen or cavity where foam is desired. In certain embodiments, a "lava-like" foam which tends to adhere to the delivery catheter 2200 is deployed; in these embodiments, the foam is optionally detached by rotating the delivery catheter 2200 prior to its retraction.

In certain cases where a "lava-like" foam is used, it may be desirable to utilize a delivery catheter with a detachable distal portion rather than detaching the foam from the catheter tip, for example to minimize the application of force to the inner wall of an unstable aneurysm. In the embodiment of FIG. 23, the delivery catheter 2300 includes a detachable tip 2310 which includes at least one aperture (in this case a side aperture 2320) for dispensing the in situ foaming formulation. In use, after the foam is dispensed, the detachable tip is detached from the rest of the delivery catheter 2300. The detachable tip 2310 may be attached to the rest of the delivery catheter 2300 using any suitable means known in the art (e.g. mechanical means, dissolvable adhesive, a removable wire connection, a threaded interface, or an electrolytically severable connecting portion, etc.).

In other embodiments, the delivery catheter includes a detachable portion which is not necessarily the same portion used to deliver the in situ foaming formulation. For instance, in the exmbodiment shown in FIG. 24, the delivery catheter 2400 includes a detachable cage 2410 that acts as a scaffold for the foam dispensed from the catheter. The cage is preferably shaped to resist displacement, e.g. by fluid flows within the lumen or aneurysm, and/or to guide the final shape of the foam, for instant to direct the accumulation of foam and, thereby, the application of pressure by the foam to the internal wall of the lumen or cavity. The cage is preferably formed of a hemocompatible material such as nitinol, steel, or plastic. The cage defines a plurality of pores which are generally between 0.1 and 1.0 mm. In use, the formulation is dispensed through the catheter and around the cage to form an embolic plug; after the plug is formed, the cage 2410 is detached and the catheter 2400 is retracted.

In some embodiments, a polymer coil or fiber is used as a scaffold for the foam. The fiber or coil is optionally delivered through a delivery catheter in parallel with the in situ foaming formulation and remains at least partially within the catheter, thereby resisting migration due to the flow of fluid around the catheter. As it is delivered, the fiber or coil preferably achieves close apposition with at least a portion of the inner wall of the lumen or cavity, and optionally exerts a radially outward or other force so that the fiber or coil remains in place.

In other embodiments, the fiber or coil is deployed within the lumen or cavity before the formulation is dispensed. In these embodiments, the deployed fiber or coil preferably applied a retentive force on the inner wall of the cavity of the lumen into which the formulation will be delivered. For instance, the coil or fiber, in certain embodiments, applied a radially outward force to the inner wall of the cavity or lumen, while in other embodiments the fiber or coil includes a retention feature such as a hook.

Delivery catheters according to various embodiments of the invention also optionally include one or more features for ensuring that a precise volume of formulation is delivered. In cases where the delivery catheter is not pre-filled with the formulation, it may be difficult to ensure that precise volumes are delivered; precision is enhanced by features that expel all of the formulation from the delivery catheter. In some embodiments, delivery catheters of the invention include a plunger, which is sized to occupy substantially all of the cross-sectional area of the delivery catheter and which optionally has a hydrophobic surface that does not stick to the in situ foaming formulation. The plunger may have a generally planar or a non-planar (e.g. conical) profile and is mounted on a structure that is sufficiently rigid to allow advancement and retraction of the plunger within the catheter (e.g. a wire or metal coil). In use, to evacuate the catheter of its contents, the plunger is passed through the lumen of the catheter toward the distal end; after the plunger is advanced through substantially all of the length of the catheter, the catheter is then moved to a new site where delivery of a foam is desired or withdrawn.

Detachment of "lava-like" and other adhesive foams from delivery catheters of the invention may be facilitated by mechanical means. Turning to FIG. 25, the delivery catheter 2500 includes an inner and outer catheter 2510, 2520 as described above. The inner catheter 2510 includes, at its distal tip, at least one cutting member 2511 that is moveable between an open configuration when the inner catheter 2510 is extended from the outer catheter 2520 (FIG. 25A) and a closed configuration when the inner catheter 2510 is retracted into the outer catheter 2520 (FIG. 25B).

In some cases, a valve may be disposed at a distal end of a delivery catheter in order to regulate the flow of in situ foaming formulation out of the catheter and into the body and/or to prevent fluids such as water from entering the catheter, where it might react with the formulation and occlude the catheter. Thus, delivery catheters according to certain embodiments of the invention are valved to regulate inflows and/or outflows. Valves used in these embodiments may be of any type currently known in the art, including duckbill valves, diaphragm valves, ball valves, etc. In order to accommodate guidewires, catheters according to these embodiments optionally include a separate guidewire lumen, either inside or outside of the delivery lumen of the catheter.

Referring now to FIG. 26, a delivery catheter 2600 includes a delivery sheath or outer catheter 2610 and a delivery (or inner) catheter 2620. The distal end of the inner catheter 2620 includes a duckbill valve 2630 oriented to permit fluid to flow out of the catheter, but to prevent fluid from flowing in. Delivery catheter 2600 is able to accommodate a guidewire: to position the catheter, the guidewire is advanced within a body lumen to a site where foam is desired to be delivered, then the outer catheter 2610 is advanced over the wire to the site. The guidewire is then withdrawn and the inner catheter 2620 is advanced through the inner sheath to the site, at which point the formulation is flowed out of the catheter and into the site.

Other embodiments of the invention utilize diaphragm valves comprising an impermeable elastic membrane having one or more slits therethrough. When the valve has the "X" shaped slit, a guidewire can be passed through the valve without risk of damage. The valve is preferably sized and shaped so that it opens in response to the application of a threshold pressure that is above the fluid pressure within the lumen (e.g. the patient's blood pressure, where the catheter is used to treat an aneurysm).

Irrespective of their design, valves for use in delivery catheters of the invention are secured to the delivery catheters using any suitable means known in the art, including through adhesives, friction fit, ultrasonic welds, heat-bonding, etc. In some cases, such as that shown in FIG. 27, the delivery catheter 2700 includes a valve 2710 and a shape memory structure 2720 adapted to exert a radially-outward force on the catheter. The valve 2710 may be formed integrally with the shape memory structure 2720, or it may include a lip or other portion which is designed to be interposed and pinched between the shape memory structure 2720 and the inner wall of the delivery catheter 2700. The shape memory structure 2720 is optionally held in place with hooks 2730 or protrusions 2740 formed on the inner surface of the catheter 2700.

Turning to FIG. 28, certain embodiments of the invention incorporate more complex two-way valves. For instance, the delivery catheter 2800 includes a distal aperture 2810 as well as a plurality of side apertures 2820. The distal aperture 2810 is sealed with a duckbill valve 2811 that prevents the outflow of fluid while permitting inflows (i.e. opening to negative pressure within the catheter) to accommodate the retraction of a guidewire. Side apertures 2820 meanwhile are sealed by one-way valves 2821 such as umbrella valves, reed valves or diaphragm valves that prevent inflow while permitting outflow (i.e. opening to positive pressure within the catheter). In preferred embodiments, the duckbill valve 2811 is oriented to direct formulation toward the side apertures 2820.

FIG. 29 depicts yet another valve embodiment in which the delivery catheter 2900 is delivered with an open lumen, optionally over a guidewire, but includes a barrier member such as a ball 2910 disposed within the lumen of the catheter to prevent the flow of in situ foaming formulation through the distal aperture 2920. The distal end of the catheter includes a portion 2921 with an inner diameter that is less than a diameter of the ball 2910, to prevent the ball from traveling through the distal aperture 2910. The ball is also optionally removable and redeployable through the application of negative and positive pressure within the lumen. The catheter 2900 also includes one or more side apertures 2930 through which the formulation can flow once the ball 2910 has advanced to the distal tip of the catheter 2900.

Fluid Systems that Minimize Formulation Breakaway

It is desirable, when dispensing in situ foaming formulations, to dispense them as unified boluses of material in order to form unified foam bodies within body lumens or cavities. When the formulation is broken up during delivery, the resulting foams may be comprised of multiple heterogenous foams of different sizes, which may be prone to displacement and/or migration within the body lumen; this in turn could lead to undesirable side effects such as unwanted embolization of small vessels near the site of foam delivery.

While not wishing to be bound to any theory, it is believed that one cause of the breakup of formulations is the presence of dead spaces within the flow path of the formulations, e.g. the tubing connecting a reservoir of formulation (e.g. in a double-barrel syringe) to the delivery catheter. For instance, currently used catheter hubs include dead space that permits flush fluid to become trapped when more viscous fluids (such as in situ foaming formulations) are injected therethrough. This effect is more pronounced at higher flow rates, particularly those greater than 1 ml/min (See FIG. 30A—formulation is clear, flush is dark). However, at flow rates below 1 ml/min, stable interfaces can generally form between viscous formulations and non-viscous flush fluids, as shown in FIG. 30B. Accordingly, in certain embodiments of the invention, delivery systems such as those described above include syringe pumps, valves other regulators of flow that prevent flow rates from exceeding 1 ml/min.

Again, while not wishing to be bound by any theory, it is generally understood that, as rates of flow increase within a tube comprising an interface between a viscous and non-viscous fluid, the leading edge of the viscous fluid deforms from a more planar meniscus to a more parabolic meniscus which may trap the less viscous fluid near the edges of the tube. The potential for less viscous fluid to be trapped is greater in places where dead space exists, for example within catheter hubs or luer connections which rapidly transition from large crosssectional areas such as those of conventional female luer connectors to small cross sectional areas such as those of male luer tips. Accordingly, certain embodiments of the invention reduce the likelihood that flush fluid will be trapped by an advancing formulation meniscus and minimize dead spaces by providing smooth and progressive tapering from large to small diameter portions. Turning to FIGS. 31 and 32, catheter hubs and fluid connectors 3100 (e.g. luer connectors) according to various embodiments of the invention include at least one female end 3110 characterized by a first inner diameter and at least one male end 3120 characterized by a second inner diameter less than the first inner diameter. The female and male ends 3110, 3120 are connected by a fluid flow path 3130 that tapers smoothly and continuously from the first diameter to the second diameter, eliminating dead spaces caused by more sudden changes in diameter. The fluid flow 3130 path has, in various embodiments such as the one shown in FIG. 31, a symmetrical taper in which each of the female and male ends 3110, 3120 and the flow path 3130 share a single central axis. In other embodiments, such as the one shown in FIG. 32, the female and male ends 3110, 3120 are offset relative to one another, and the flow path 3130 has an eccentric taper. Embodiments utilizing an eccentric taper advantageously delay the leading edge of the meniscus from entering the male end 3120 and promote flattening of the formulation meniscus, thereby minimizing the trapping of flush fluid within the formulation.

CONCLUSION

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The various embodiments described herein have focused on the use of aspects of the present invention in "lumens," "cavities" or "sacs." The term "lumen" as used herein refers to the space defined by a tubular structure within the body, including without limitation a blood vessel, an intestine, a bronchus, or a long bone. The term "cavity" as used herein refers to any space within a body structure, whether or not a lumen. Exemplary cavities include, without limitation, the peritoneal cavity, the abdominal cavity, the oral cavity, a sinus cavity, a cyst, a chamber of the heart, etc. The term "sac" as used herein refers generally to a cavity that is filled with a material such as fluid, for instance (without limitation) an aneurysm sac, the greater sac, the lesser sac, the bladder, etc.) It will be understood by those of skill in the art that these terms may overlap in meaning, and that certain structures may be described by one, two or all three of these terms.

The term "consists essentially of means excluding other materials that contribute to function, unless otherwise defined herein. Nonetheless, such other materials may be present, collectively or individually, in trace amounts.

As used in this specification, the term "substantially" or "approximately" means plus or minus 10% (e. g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system for treating a patient, comprising:
an endoprosthesis configured to span an aneurysm characterized by a top and a bottom; and
a formulation adapted to form a polymer foam when exposed to blood,
wherein the formulation is configured to flow outward from a catheter tip and form an expanding mass in a space between the endoprosthesis and a wall of the aneurysm and wherein the formulation is a siloxane formulation that reacts with the blood in situ and expands no more than 1.3 times the original volume of the formulation: and
wherein the formulation is configured to have a density greater than the density of blood, sinks toward the bottom of the aneurysm when disposed therein and generates a foam that expands upward in the aneurysm; or
the formulation is configured to have a density less than that of blood, floats toward the top of the aneurysm when disposed therein and generates a foam that expands downward in the aneurysm.

2. The system of claim 1, wherein the formulation is configured to float in blood and the formulation, when disposed within the aneurysm, floats to the top and generates a foam that expands to occupy at least a portion of the volume of the aneurysm from the top down.

3. The system of claim 2, further comprising a catheter having a tip that is positionable at the bottom of the aneurysm, wherein the catheter is configured to permit at least one of the discharge of the formulation into the aneurysm and the inflow of blood displaced by a downward expansion of the foam.

4. The system of claim 3, wherein the catheter includes a first lumen configured to discharge the formulation into the aneurysm and a second lumen configured to permit the inflow of blood displaced by the downward expansion of the foam.

5. The system of claim 3, wherein the tip of the catheter is sized to fit within a lumbar artery.

6. The system of claim 3, wherein the tip of the catheter is sized to fit through one of a fenestration within the endoprosthesis and a space between the endoprosthesis and a blood vessel fluidly connected to the aneurysm.

7. The system of claim 3, wherein the tip of the catheter includes a retractable shield adapted to inhibit the migration of the formulation from the top of the aneurysm toward the bottom.

8. The system of claim 1, wherein the endoprosthesis is a stent graft.

9. The system of claim 1, wherein the endoprosthesis is a catheter balloon and is configured to be removed after a foam has been formed between an outer surface of the catheter balloon and an inner surface of the aneurysm.

10. The system of claim 1, wherein the formulation has a density greater than that of blood and the formulation, when disposed within the aneurysm, sinks to the bottom and generates a foam that expands to occupy at least a portion of the volume of the aneurysm from the bottom up.

11. The system of claim 10, further comprising a catheter having a tip that is positionable at the top of the aneurysm, wherein the catheter is configured to permit at least one of the discharge of the formulation into the aneurysm and the inflow of blood displaced by an upward expansion of the foam.

12. The system of claim 11, wherein the catheter includes a first lumen configured to discharge the formulation into the aneurysm and a second lumen configured to permit the inflow of blood displaced by the upward expansion of the foam.

13. The system of claim 11, wherein the tip of the catheter is sized to fit within an inferior mesenteric artery.

14. The system of claim 11, wherein the tip of the catheter is sized to fit through one of a fenestration within the endoprosthesis and a space between the endoprosthesis and a blood vessel fluidly connected to the aneurysm.

15. The system of claim 11, wherein the tip of the catheter includes a retractable shield adapted to inhibit the migration of the formulation from the bottom of the aneurysm toward the top.

16. The system of claim 10, wherein the endoprosthesis is a catheter balloon and is configured to be removed after a foam has been formed between an outer surface of the catheter balloon and an inner surface of the aneurysm.

17. The system of claim 1, wherein the endoprosthesis is a stent graft.

18. A system for treating a patient, comprising:
an endoprosthesis configured to span an abdominal aortic aneurysm;
a formulation configured to form a polymer foam within the abdominal aortic aneurysm, wherein the formulation is a siloxane formulation that reacts with the blood in situ; and
wherein the formulation is formulated to have a density greater than the density of blood, sinks toward the bottom of the abdominal aortic aneurysm when disposed therein and generates a foam that expands upward in the aneurysm,
or is formulated to have a density less than that of blood, and when disposed within the abdominal aortic aneurysm, floats toward the top of the abdominal aortic aneurysm and expands downward in the aneurysm; and
a delivery catheter having a tip and insertable through one of an inferior mesenteric artery, a lumbar artery, a fenestration within the endoprosthesis and a space between the endoprosthesis and a wall of a blood vessel adjoining the abdominal aortic aneurysm,
wherein the formulation is configured to flow outward from the catheter tip and to occupy a predetermined location within the aortic aneurysm prior to expansion and form an expanding mass that expands in a predetermined direction therefrom in the space between the endoprosthesis and the wall of the blood vessel and expands no more than 1.3 times the original volume of the formulation.

19. The system of claim 18, wherein the formulation has a density less than that of blood.

20. The system of claim 18, wherein the formulation has a density that is greater than that of blood.

* * * * *